United States Patent [19]
Tulshian et al.

[11] Patent Number: 5,939,419
[45] Date of Patent: *Aug. 17, 1999

[54] 2-BENZYL-POLYCYCLIC GUANINE DERIVATIVES AND PROCESS FOR PREPARING THEM

[75] Inventors: Deen Tulshian, Lebanon; Brian A. McKittrick, Bloomfield; Yan Xia, Edison; Samuel Chackalamannil, East Brunswick, all of N.J.

[73] Assignee: Schering-Plough Corporation, Kenilworth, N.J.

[*] Notice: This patent is subject to a terminal disclaimer.

[21] Appl. No.: 08/507,508

[22] PCT Filed: Feb. 24, 1994

[86] PCT No.: PCT/US94/01728

§ 371 Date: Nov. 26, 1996

§ 102(e) Date: Nov. 26, 1996

[87] PCT Pub. No.: WO94/19351

PCT Pub. Date: Sep. 1, 1994

Related U.S. Application Data

[63] Continuation-in-part of application No. 08/024,599, Feb. 26, 1993, abandoned, and a continuation-in-part of application No. 08/023,549, Feb. 26, 1993, abandoned.

[51] Int. Cl.⁶ ............ C07D 487/14; C07D 487/20; C07D 491/22; A61K 31/505
[52] U.S. Cl. ............ 514/257; 544/247; 544/251
[58] Field of Search ............ 514/257; 544/247, 544/251, 252

[56] References Cited

U.S. PATENT DOCUMENTS

| | | | |
|---|---|---|---|
| 4,469,698 | 9/1984 | Philippossian et al. | 424/253 |
| 4,663,446 | 5/1987 | Wright | 536/28 |
| 4,670,438 | 6/1987 | Austel et al. | 514/249 |
| 4,722,929 | 2/1988 | Austel et al. | 514/303 |
| 5,185,341 | 2/1993 | Sauer et al. | 514/269 |
| 5,264,573 | 11/1993 | Ramert et al. | 544/265 |
| 5,270,316 | 12/1993 | Suzuki et al. | 514/267 |

FOREIGN PATENT DOCUMENTS

| | | |
|---|---|---|
| 39780 | 11/1981 | European Pat. Off. |
| 45094 | 2/1982 | European Pat. Off. |
| 149200 | 7/1985 | European Pat. Off. |
| 184738 | 6/1986 | European Pat. Off. |
| 423805 | 4/1991 | European Pat. Off. |
| 466164 | 1/1992 | European Pat. Off. |
| WO 91/19717 | 12/1991 | WIPO. |

OTHER PUBLICATIONS

Khmelevskii et al, *J. Gen. Chem., USSR* 28 (1958), pp. 2016–2020.
Branfman et al, *Drug Metab. and Disposition*, 11 (1983), pp. 206–210.
Baum et al, *J. Cardiovasc. Pharmacol.*, 5, 4 (1983), pp. 655–667.
*Chemical Abstracts*, 81, (1974) abstract 62626q.
*Chemical Abstracts*, 98, (1983) abstract 174511f.
*Chemical Abstracts*, 116, (1992) abstract 209475s.
*Chemical Abstracts*, 110, (1989) abstract 2572b.
Pfleiderer, *Liebigs Ann. Chem.*, (1974), pp. 2030–2045.
*Chemical Abstracts*, 99, (1983) abstract 100b.
Bergmann et al, *J. Chem. Soc.*, (1964), pp. 565–572.
*Chemical Abstracts*, 67, (1967) abstract 54153d.
*Chemical Abstracts*, 108, (1988) abstract 94267r.
Fu et al, *J. Heterocyclic Chem.*, 3 (1966), pp. 476–481.
Fraisse et al, *J. Med. Chem.*, 36 (1993), pp. 1465–1473.
Muller et al, *J. Med. Chem.*, 36 (1993), pp. 3341–3349.
*Chemical Abstracts*, 119, (1993) abstract 197329u.
Lister, "Part II, Purines," *Fused Pyrimidines*, ed. Brown (New York: Wiley–Interscience, 1971), pp. 47–51.

*Primary Examiner*—Mukund J. Shah
*Assistant Examiner*—Deepak R. Rao
*Attorney, Agent, or Firm*—Anita W. Magatti

[57] ABSTRACT

Antihypertensive and bronchodilating compounds of the formula

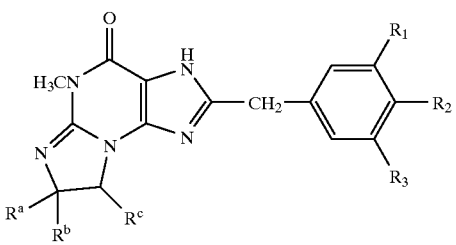

or a pharmaceutically acceptable salt thereof, and a process for preparing them are disclosed, wherein:

$R_1$, $R_2$, $R_3$, $R^a$, $R^b$ and $R^c$ as defined in the disclosure;

pharmaceutical compositions containing said compounds;

methods of treatment using said compounds; and a process for preparing polycyclic guanines comprising
a) reducing a nitrosopyrimidine, and treating the reduced nitrosopyrimidine with an acylating reagent to give the amidopyrimidine;
b) reacting the amidopyrimidine with a halogenating/cyclizing reagent to give a halopurine;
c) reacting, in the presence of a base, the halopurine with an amine to give the substituted aminopurine; and
d) closing the ring of the substituted aminopurine with a suitable dehydrating agent.

9 Claims, No Drawings

2-BENZYL-POLYCYCLIC GUANINE DERIVATIVES AND PROCESS FOR PREPARING THEM

The present application is the United States national application corresponding to International Application No. PCT/US 94/01728, filed Feb. 24, 1994 and designating the United States, which PCT application is in turn a continuation-in-part of U.S. application Ser. No. 08/024599, filed Feb. 26, 1993 and 08/023549 filed Feb. 26, 1993 both of which are now abandoned.

BACKGROUND

The present invention relates to 2-benzyl-polycyclic guanine derivatives useful for treating cardiovascular and pulmonary disorders, as well as to their pharmaceutical compositions, methods for using the same and a process for preparing them. Most compounds of this invention were generically but not specifically disclosed in PCT publication WO91/19717, published Dec. 26, 1991. We have found that the compounds of the present invention show unexpectedly superior cardiovascular and pulmonary activity compared to the compounds of the prior publication.

SUMMARY OF THE INVENTION

The present invention is directed to novel 2-benzyl-polycyclic guanine derivatives of the formula:

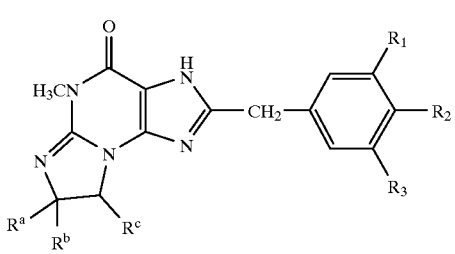

I or a pharmaceutically acceptable salt thereof, wherein:

$R_1$, $R_2$ and $R_3$ are independently selected from the group consisting of hydrogen, lower alkyl, lower alkoxy, halogeno, hydroxy, (di-lower alkyl)amino, 4-morpholinyl, 1-pyrrolidinyl, 1-pyrrolyl, —$CF_3$, —$OCF_3$, phenyl and methoxyphenyl; or $R_1$ and $R_2$ together are methylenedioxy; or $R_1$ and $R_2$ together with the carbon atoms to which they are attached form a benzene ring; and $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5–7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5–7 carbons.

Preferred compounds are those wherein $R_1$ and $R_3$ are hydrogen. More preferred are compounds wherein $R_1$ and $R_3$ are hydrogen and $R_2$ is hydrogen, —$OCF_3$, methyl, methoxy, fluoro, phenyl, methoxyphenyl, dimethylamino, 1-pyrrolidinyl or 1-pyrrolyl, and compounds wherein $R_1$ and $R_2$ together are methylenedioxy and $R_3$ is hydrogen.

Also preferred are compounds wherein $R^a$ is hydrogen and $R^b$ and $R^c$, together with the carbon atoms to which they are attached, form a saturated ring of 5 carbons; compounds wherein $R^a$ is lower alkyl, $R^b$ is hydrogen or lower alkyl, and $R^c$ is hydrogen; compounds wherein $R^a$ and $R^b$ and the carbon atom to which they are attached form a saturated ring of 5 carbons and $R^c$ is hydrogen; compounds wherein $R^a$ is hydrogen and $R^b$, $R^c$ and the carbon atoms to which they are attached form a tetrahydrofuran ring; and compounds wherein $R^a$ and $R^b$, together with the carbon atoms to which they are attached, and $R^b$ and $R^c$, together with the carbon atoms to which they are attached, each form a saturated ring of 5 carbons. More preferred are compounds wherein $R^a$ is hydrogen and $R^b$ and $R^c$, together with the carbon atoms to which they are attached, form a saturated ring of 5 carbons; compounds wherein $R^a$ and $R^b$ and the carbon atom to which they are attached form a saturated ring of 5 carbons and $R^c$ is hydrogen; and compounds wherein $R^a$ is lower alkyl, $R^b$ is hydrogen or lower alkyl, and $R^c$ is hydrogen.

Of compounds of formula I wherein $R^a$ is hydrogen and $R^b$ and $R^c$, together with the carbon atoms to which they are attached, form a saturated ring of 5 carbons, most preferred are compounds wherein $R_1$, $R_2$ and $R_3$ are as listed in the following table:

| $R_1$ | $R_2$ | $R_3$ |
|---|---|---|
| H | H | H |
| H | F | H |
| H | —$OCH_3$ | H |
| H | —$CH_3$ | H |
| H | $(CH_3)_2N$— | H |
| H | $C_6H_5$— | H |
| H | —$OCF_3$ | H |
| H | —N⟨pyrrolidinyl⟩ | H |
| H | —N⟨pyrrolyl⟩ | H |
| 3,4-$OCH_2O$— | | H |
| H | —$C_6H_4OCH_3$ | H |

The compounds of formula I are useful as antihypertensive, bronchodilating and blood platelet inhibiting agents. Compounds of the invention are useful in inhibiting phosphodiesterase enzymes; the inhibition of vascular phosphodiesterase is associated with vasodilation and vasorelaxation, and therefore is expected to induce antihypertensive and antianginal activity. Compounds of formula I can also serve as smooth muscle relaxants and are therefore useful in the treatment of bronchoconstriction. Such compounds also can inhibit smooth muscle proliferation, vascular growth and platelet function and are useful in treating conditions such as restenosis post angioplasty, atherosclerosis and conditions which benefit from inhibiting platelet function. Through one or more of the above physiological mechanisms, compounds of formula I are also useful in treating ischemia and peripheral vascular diseases.

The present invention is also directed toward a pharmaceutical composition containing a compound of formula I in an amount effective to inhibit phosphodiesterase enzymes, smooth muscle proliferation, vascular growth or platelet function, or to relax smooth muscle. The present invention is also directed toward a pharmaceutical composition containing an anti-hypertensive, an anti-anginal, a bronchodilating or a platelet inhibiting effective amount of a compound of formula I.

The present invention is also directed toward a method for treating hypertension, angina, bronchoconstriction, restenosis post angioplasty, atherosclerosis, ischemia, peripheral vascular diseases, or diseases benefitting from platelet inhibition in a mammal comprising administering to a mammal in need of such treatment an amount of a compound of formula I effective to treat any of the above diseases. The present invention is also directed toward a method for maintaining guanosine 3':5'-cyclic monophosphate (cGMP) levels in a mammal by administering an amount of a compound of formula I effective to maintain or increase cGMP levels.

In another embodiment, the present invention is directed toward the preparation of a polycyclic guanine of formula II

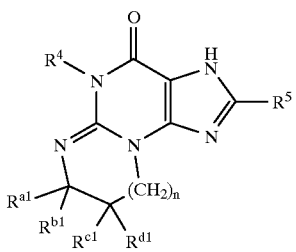

II wherein, $R^4$ is H, alkyl or alkyl substituted with aryl or —OH;

$R^5$ is H, halo, —$CF_3$, alkoxy, alkylthio, alkyl, cycloalkyl, —$SO_2NH_2$, —$NH_2$, monoalkylamino, dialkylamino, hydroxyalkylamino, aminoalkylamino, —COOH, alkoxycarbonyl, aminocarbonyl, aryl, substituted aryl or alkyl substituted with aryl, substituted aryl, —OH, alkoxy, —$NH_2$, monoalkylamino or dialkylamino;

$R^{a1}$, $R^{b1}$, $R^{c1}$ and $R^{d1}$ independently represent H, alkyl, cycloalkyl or aryl; or ($R^{a1}$ and $R^{b1}$) or ($R^{c1}$ and $R^{d1}$) or ($R^{b1}$ and $R^{c1}$) can complete a saturated ring of 5- to 7-carbon atoms, or ($R^{a1}$ and $R^{b1}$) taken together and ($R^{b1}$ and $R^{c1}$) taken together, each complete a saturated ring of 5- to 7-carbon atoms, wherein each ring optionally can contain a sulfur or oxygen atom and whose carbon atoms may be optionally substituted with one or more or the following: alkenyl, alkynyl, —OH, —COOH, alkoxycarbonyl, alkyl or alkyl substituted with —OH, —COOH or alkoxycarbonyl; or such saturated ring can have two adjacent carbon atoms which are shared with an adjoining aryl ring; and n is zero or one;

wherein the process comprises:
a) reducing a nitrosopyrimidine (III), and treating the reduced nitrosopyrimidine with an acylating reagent (IV), optionally in the presence of either an acylating catalyst and/or coupling reagent and/or phase transfer catalyst to give the amidopyrimidine (V);
b) reacting the amidopyrimidine (V) with an effective amount of a halogenating/cyclizing reagent, optionally in the presence of one or more additional halide sources, and also optionally in the presence of a phase transfer catalyst to give a halopurine (VI);
c) reacting, in the presence of a base, the halopurine (VI) with an amine of the formula:

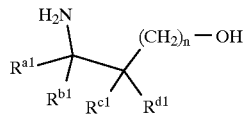

(VII)

wherein $R^{a1}$, $R^{b1}$, $R^{c1}$, $R^{d1}$ and n are as described above to give the substituted aminopurine (VIII);
d) closing the ring of the substituted aminopurine (VIII) with a suitable dehydrating agent to give the polycyclic guanine (II).

In another embodiment, the present invention is directed toward a process for preparing amidopyrimidines of formula V, comprising: reducing a nitrosopyrimidine of formula III, and treating the reduced nitrosopyrimidine with an acylating reagent, optionally in the presence of either an acylating catalyst and/or coupling reagent and/or phase transfer catalyst. This process corresponds to step a) above.

In another embodiment, the present invention is directed toward a process for preparing a halopurine of formula VI, comprising reacting an amidopyrimidine (V) with an effective amount of a halogenating/cyclizing reagent, optionally in the presence of one or more additional halide sources, and also optionally in the presence of a phase transfer catalyst. This process corresponds to step (b) above. This process can further include step (c) and/or step (d), described below.

In another embodiment, the present invention is directed toward a process for preparing a substituted aminopurine of formula VIII, comprising reacting, in the presence of a base, the halopurine (VI) with an amine of the formula:

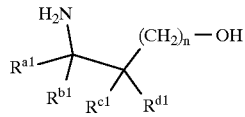

VII wherein $R^{a1}$, $R^{b1}$, $R^{c1}$, $R^{d1}$ and n are as described above. This process corresponds to step c) above. This process can further comprise step (d), described below.

The present invention is also directed toward the novel intermediates: amidopyrimidine V, halopurine VI and aminopurine VIII, with the proviso that with regards to amidopyrimidine V, where Z is =O, $R^4$ and $R^5$ cannot both be methyl.

The present invention has the advantage of providing a process for preparing polycylic guanine derivatives and intermediates thereof, in as few or even fewer steps than other processes previously taught, in good yields with little formation of undesirable by-products, with less waste to dispose of or recycle. The present invention has the further advantage of providing novel intermediates which enable the above process to achieve these advantages.

DETAILED DESCRIPTION OF THE INVENTION

In describing the present invention, "lower alkyl" represents a straight alkyl chain having from 1 to 6 carbon atoms or a branched alkyl chain of 3 to 6 carbon atoms, for example methyl, ethyl, propyl, isopropyl, butyl, isobutyl, tert-butyl, pentyl and hexyl.

"lower alkoxy" represents an alkoxy group wherein the alkyl portion is as defined above, for example, methoxy, ethoxy, propoxy, pentyloxy and hexyloxy.

"Halogeno" represents fluoro, chloro, bromo or iodo.

"Aryl" represents a carbocyclic moiety containing at least one benzenoid-type ring, with the aryl moiety having from 6 to 14 carbon atoms, with all available substitutable carbon atoms of the aryl moiety being intended as possible points of attachment, for example phenyl, naphthyl, indenyl, indanyl and the like.

"Substituted aryl" represents an aryl moiety as defined above substituted with 1 to 3 substituents selected from the group consisting of halogeno, lower alkyl, —$CF_3$, —$OCF3$, phenyl, —OH, lower alkoxy, phenoxy, amino, (mono-lower alkyl)amino, (di-lower alkyl)amino, 4-morpholinyl, 1-pyrrolidinyl, 1-pyrrolyl and methoxyphenyl, or substituents on adjacent carbon atoms form a methylenedioxy group.

Certain compounds of the invention e.g., those with a basic nitrogen containing moiety, can also form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner.

Certain compounds of the invention will be acidic in nature, e.g., those compounds which possess a carboxy or phenolic hydroxyl group. These compounds may form pharmaceutically acceptable salts. Examples of such salts are the sodium, potassium, calcium, aluminum, gold and silver salts. Also contemplated are salts formed with pharmaceutically acceptable amines such as ammonia, alkylamines, hydroxyalkylamines, N-methylglucamine and the like.

Compounds of formula I form enantiomers, with the (+) enantiomeric form being preferred. For example, the preferred stereochemistry for compounds wherein $R^a$ is hydrogen and $R^b$ and $R^c$, together with the carbon atoms to which they are attached, form a saturated ring of 5 carbons is shown in the following partial structural formula:

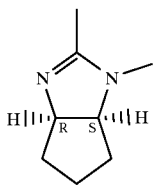

The process aspect of the present invention and its various embodiments are illustrated below:

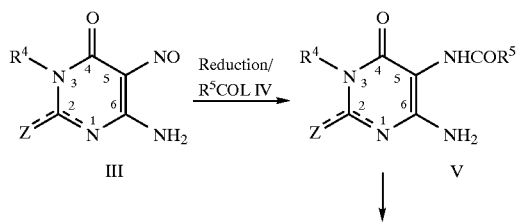

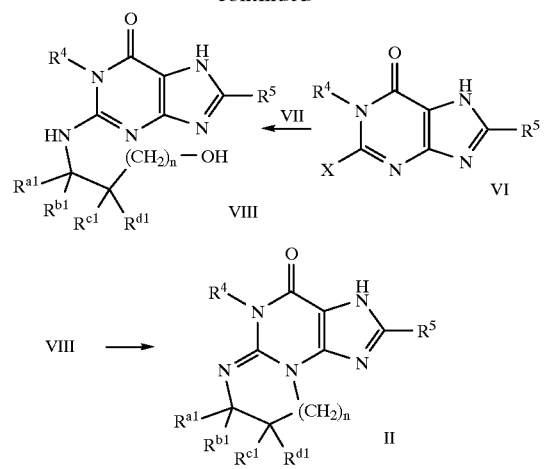

wherein $R^4$, $R^5$, $R^{a1}$, $R^{b1}$, $R^{c1}$, $R^{d1}$ and n are as defined above;

L is a leaving group;

X is halogeno;

Z is =O or —$OR^6$, wherein $R^6$ is alkyl; and the dotted lines "---" indicate an optional double bond such that when Z is =O, position 1 contains hydrogen and there is single bond between positions 1 and 2 on the ring, or when Z is —$OR^6$ wherein $R^6$ is alkyl, there is a double bond between positions 1 and 2 on the ring;

The amidopyrimidines of formula V can be prepared by reducing a nitrosopyrimidines of formula III, followed by treatment with an acylating reagent. Suitable reducing agents include hydrogen with a metal catalyst, such as the metals from Group VIII of the periodic table or salts or complexes thereof, or a mixture of metal of Group VIII with carbon. Suitable metals include platinum, palladium, nickel, rhodium, ruthenium or mixtures thereof. The reduced nitrosopyrimidine is then treated with an acylating reagent, optionally in the presence of either an acylating catalyst and or coupling reagent and/or phase transfer catalyst. In the reduction of nitrosopyrimidines, the metal catalyst can be employed in amounts effective to give the reduced nitrosopyrimidine. Such amounts can range from about 1 to about 200 mole percent of the metal catalyst, preferably from about 1 to about 50 mole percent, more preferably about 1 to about 20 mole percent metal catalyst. Reduction can be carried out at temperatures effective to give the the reduced nitrosopyrimidine, and can range from about −40° C. to about 100° C., more preferably from about 0° to about 50° C., more preferably from 10° to 30° C. The nitrosopyrimidine of formula III is reduced under pressures ranging from about ambient to about 400 pounds per square inch (psi) (20 kilotorr), preferably from about 35 psi (1.8 kilotorr) to 100 psi (5.1 kilotorr), more preferably from about 50 psi (2.6 kilotorr) to 70 psi (3.6 kilotorr). The nitrosopyrimidine (III) can be reduced for a time sufficient to allow the desired completion of the reaction, such as from 10 minutes to one week or more, preferably from about 5 to 48 hours.

Suitable acylating reagents include anhydrides, organic acid halides, mixed anhydrides, activated acid esters, organic acids or mixtures thereof of the formula $R^5$COL (IV) wherein $R^5$ is as defined before, and L represents a leaving group, such as an anhydride, a halide or an activated ester. Representative acylating reagents include acetic acid (HOAc), acetyl chloride, acetyl bromide, acetic anhydride, benzoyl chloride, aryl substituted arylacetic acids or derivatives such as para-trifluorophenylacetyl chloride, para-dimethylaminophenylacetyl chloride and para-trifluorophenyl acid. Other acylating agents can include aryl substituted aryl acetic acid chlorides and anhydrides; or can include acetic acid derivatives of formula 2 described in Route 1. The acylating reagents can be employed in amounts effective to acylate the reduced nitrosopyrimidine, and can range from about 1 to about 10 moles of acylating reagent per mole of reduced nitrosopyrimidine, preferably from about 1 to 4 moles of acylating reagent. Acylation can be carried out at temperatures effective to give the amidopyrimidine (V), and can range from about −40° C. to about 50° C., more preferably from about 0° to about 40° C. The acylation of the reduced nitrosopyrimidine can be carried out at pressures ranging from about ambient to about 400 pounds per square inch (psi) for a time sufficient to allow the desired completion of the reaction, such as from 10 minutes to 48 hours or more.

Suitable acylating catalysts include dimethylaniline, dimethylaminopyridine (DMAP) and imidazole. The acylating catalysts can be employed in amounts effective to catalyze acylation of the reduced nitrosopyrimidine. Such amounts can range from about 1 to about 20 mole percent acylating catalyst, preferably from about 1 to 10 mole percent.

Suitable coupling reagents include carbodiimides such as dicyclohexylcarbodiimide or 1-(3-dimethylaminopropyl)-3-ethylcarbodiimide hydrochloride (DEC). The latter coupling reagent may incorporate its own catalyst(s), such as benztriazoles, imidizoles, N-hydroxysuccinimides, and DMAP. The coupling reagent can be employed in an amount effective to aid acylation of the reduced nitrosopyrimidine. Such amounts can range from about 1 to about 5 moles coupling reagent, preferably from about 1 to 4 moles.

The reduction and acylation steps can be carried out in a solvent compatible with the reactants. Such solvents include ethers, water, bases, acids, dimethylformamide (DMF) or mixtures thereof. Ethers include diethylether ($Et_2O$), tetrahydrofuran (THF), tertiary butyl methyl ether (($CH_3$)$_3COCH_3$) and dimethoxyethane. Bases include hydroxides, carbonates or bicarbonates of alkali and alkaline earth metals such as lithium, sodium, potassium, magnesium, calcium or barium. Preferably the base is in the aqueous form. Acids include compounds of the formula $R^5COL$ (IV), wherein $R^5$ is as defined hereinbefore, such as HOAc, propionic acid, butyric acid, or anhydrides of any of the above acids. Alternatively, the acids can include acidic acid derivatives of formula 2 described in Route 1. Mixtures of any of the above solvents can be employed. The amount of solvent should be sufficient to provide a mixable slurry of the reactants.

Suitable phase transfer catalysts for promoting acylation in the presence of aqueous or organic media of reduced nitrosopyrimidine include tetra-substituted phosphonium salts, quaternary ammonium salts, such as tetrabutylammonium, tetramethylammonium, benzyltributylammonium, with a complementary counterion such as sulfate, hydroxide or chloride. Suitable solvents for use with the phase transfer catalysts include aliphatic hydrocarbons such as C-5 to C-20 alkanes, including heptane, or aromatic hydrocarbons such as toluene, benzene and xylenes; and chlorinated hydrocarbons such as methylene chloride ($CH_2Cl_2$), dichlorethane, chlorobenzene; or ethers such as described hereinbefore.

Amidopyrimidine V, wherein Z is =O and $R^4$ and $R^5$ are both methyl is described in A. Branfman et al., Drug Metabolism and Disposition, (1983), Vol. 11, pp. 206–210 and V. I. Khmelevskii et al. J. Gen. Chem., U.S.S.R. (1958), Vol. 28, pp. 2016–2020.

The halopurine compound of formula VI can be prepared by reacting an amidopyrimidine (V) with an effective amount of a halogenating/cyclizing reagent, optionally in the presence of one or more additional halide sources, and also optionally in the presence of phase transfer catalysts. Suitable halogenating/cyclizing reagents include phosphorous trihalide, a phosphorus pentahalide, organophosphorous halides, a phosphorus oxyhalide, thionyl halide, sulfuryl halide or mixtures thereof. The halogenating/cyclizing reagent can be employed in amounts ranging from about equimolar to excess moles per mole of amidopyrimidine, preferably from about one mole to about 50 moles of the halogenating/cyclizing reagent. The reaction can be carried out at temperatures ranging from about ambient to the boiling point of the solvent(s) employed, more preferably from about 50° C. to about 150° C. Also preferred is that the reactants are contacted at ambient pressures, although pressures greater than ambient can be employed. The reactants can be reacted for a time sufficient to allow the desired completion of the reaction, such as from 10 minutes to about one week or more.

Suitable additional halide sources include ammonium halide such as $NH_4Cl$, $NH_4Br$ or $NH_4I$, alkali metal halides such as LiCl, LiBr or LiI, halogen gases such as chlorine, bromine or iodine, and hydrogen halides such as HCl, HBr or HI. Such halide sources, together with the halogenating/cyclizing reagent, can facilitate conversion of amidopyrimidine (V) to halopurine (VI). The halide sources can be employed in amounts ranging from about 0.1 moles to excess moles per mole of amidopyrimidine, preferably from about 0.1 mole to about 5 moles.

Suitable phase transfer catalysts for converting amidopyrimidine (V) to halopurine (VI) can include those described for the above conversion of the reduced nitrosopyrimidine to amidopyrimidine. Such amounts can range from about 0.1 to about 10 moles of phase transfer catalyst per mole of amidopyrimidine, preferably from about 0.1 to about 5 moles.

The process for preparing halopurine VI can be carried out neat or with any solvent compatible with the reactants. Suitable solvents include aliphatic hydrocarbons such as C-5 to C-20 alkanes, preferably heptane, aromatic hydrocarbons such as toluene, benzene or xylenes, chlorinated hydrocarbons such as $CH_2Cl_2$, dichlorethane or chlorobenzenes, or mixtures of any of the above. Where the process is conducted neat, an excess amount of the halogenating/cyclizing reagent can be employed. The amount of solvent should be sufficient to provide a mixable slurry of the reactants.

The substituted aminopurine of formula VIII can be prepared by reacting halopurine VI with a suitable amine, optionally in the presence of an added base, optionally in the presence of phase transfer catalysts such as those described for promoting acylation. Suitable amines can be those as described in PCT/US91/04154 of the formula:

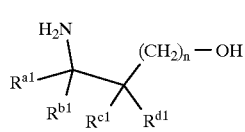

VII wherein $R^{a1}$, $R^{b1}$, $R^{c1}$, $R^{d1}$ and n are as defined above. Alternatively, the salts of amines can be employed, such as the HCl salt. The amine can be employed in amounts effective to give compound VIII, and can range from about equimolar to about 20 moles per mole of halopurine VI, preferably from about one to about four moles of amine. Suitable added bases can be either organic, inorganic or mixtures thereof. Organic bases can include nitrogen containing bases such as N-methylpyrrolidinone (NMP), triethylamine (Et$_3$N), diisopropylethylamine (iPr$_2$NEt), aniline, pyridine, 1,8-bis(dimethylamino)napthalene, polyvinyl pyridine, DMAP, dimethylaniline, leutidine, sodium tertiary butoxide and the like. It should be noted that the amine reactants described in PCT/US91/04154 can also be employed as a base. Suitable inorganic bases can include hydroxide, carbonates and bicarbonates of alkali and alkaline earth metals of Groups IA and IIA of the periodic table. Such bases can include NaOH, KOH, and sodium and potassium carbonates. The process can be carried out at temperatures effective to give the substituted aminopurine (VIII), and can range from about −20° C. to 200° C., more preferably from about ambient about 150° C. Also preferred is that the reactants are contacted at ambient pressures, although pressures greater than ambient can be employed. Optionally, the process can be carried out in a solvent compatible with the reactants. Such solvents can include any of the organic bases described above, acetonitrile (CH$_3$CN), ethers such as THF, (CH$_3$)$_3$COCH$_3$, dimethoxyethane, amides such as DMF and acetamide, aliphatic hydrocarbons such as C-5 to C-20 alkanes and chlorinated hydrocarbons as described above, or mixtures of any of the above solvents. The amount of solvent should be sufficient to provide a mixable slurry of the reactants. Optionally, the process can be carried out with phase-transfer agents, such as those defined hereinbefore.

The reactants can be contacted for a time sufficient to allow the desired completion of the reaction, such as from one to 96 hours or more, preferably from about 24 to about 72 hours.

The desired polycyclic guanine (II) can be prepared by known methods, such as those described in PCT/US91/04154. Generally, a substituted aminopurine VIII can be converted to polycyclic guanine XI by ring closure with a suitable dehydrating agent such as thionyl chloride (SOCl$_2$) or triphenylphosphine dibromide according to known procedures or procedures analogous to known procedures.

Recovery of compounds II, V, VI and VIII from the reaction mixture can be made using conventional recovery procedures, such as by extraction, crystallization, filtration and/or removal of any solvents present.

In addition to using the novel process described above, the compounds of the present invention can be prepared by several routes as described hereinafter. Variations of these routes can be employed, as well as other routes known to those skilled in the art, such as those described in WO91/19717, incorporated herein by reference.

For compounds of formula Ia wherein $R^a$ is hydrogen and $R^b$ and $R^c$, together with the carbon atoms to which they are attached, form a saturated ring of 5 carbons, the following routes 1–3 can be used:

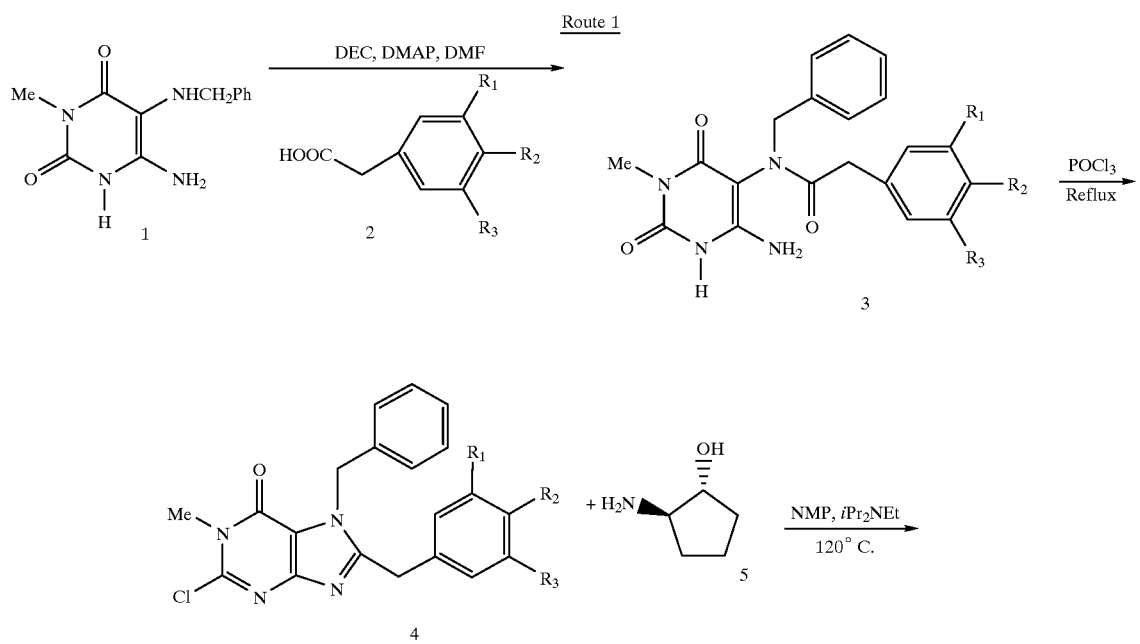

-continued

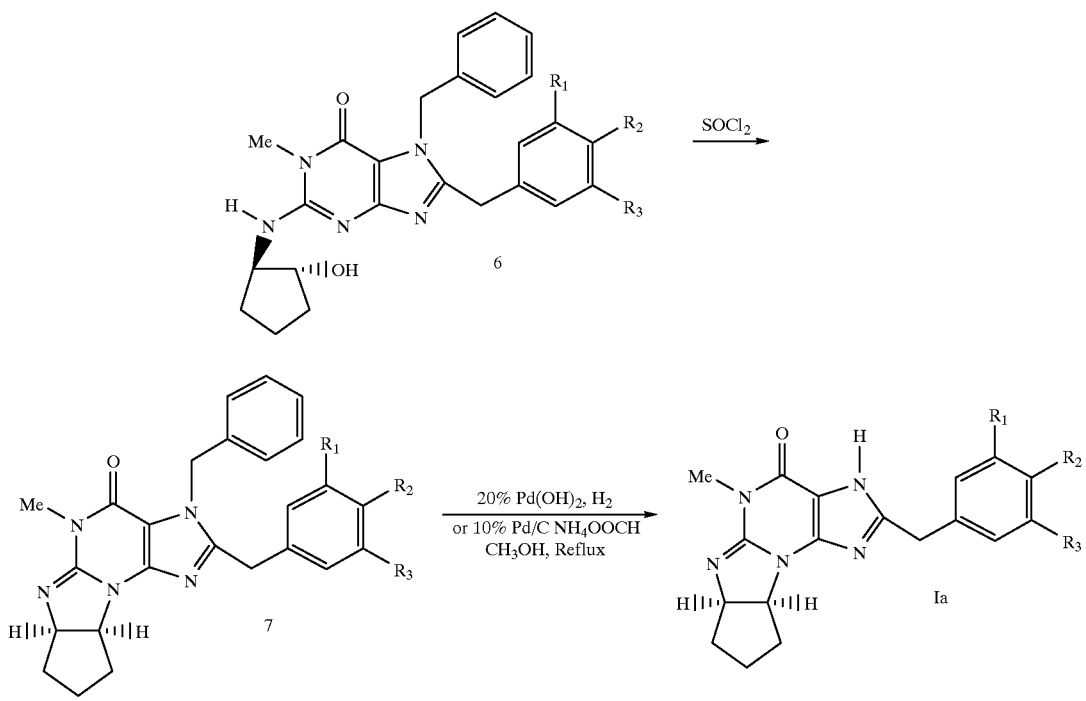

Route 1, wherein $R_1$, $R_2$ and $R_3$ are as defined above, involves coupling a uracil derivative of formula 1 with an acetic acid derivative of formula 2 using standard peptide coupling techniques, e.g. using a coupling agent such as DEC and an activating agent such as DMAP in a suitable inert solvent such as DMF. The substituted uracil derivative of formula a is then treated with a halide-forming agent such as $POCl_3$, and the resultant compound of formula 4 is aminated by reacting with trans-2-hydroxycyclopentylamine (formula 5) at elevated temperatures (100–150° C.) in the presence of i-$Pr_2NEt$ in a solvent such as NMP. The resultant compound of formula 6 is then treated with a dehydrating agent such as $SOCl_2$ to form the polycyclic ring structure of formula 7. Compounds of formula I can then be obtained by removing the amino-protecting benzyl group, e.g. by hydrogenation with a suitable palladium catalyst and hydrogen or $HCO_2NH_4$.

Starting uracil derivatives of formula 1 can be prepared by methods known in the art, for example by methods disclosed in WO91/19717. The aminoalcohol of formula 5 can be prepared by methods known in the art and by the following procedure:

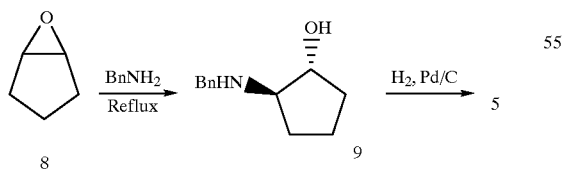

wherein Bn is benzyl. In the reaction scheme, cyclopentene oxide (8) is converted to the corresponding N-benzyl trans-hydroxycycloalkylamine of formula 9 by refluxing with benzyl amine, and the benzyl protecting group is the removed, e.g. by hydrogenation, to obtain the transhydroxycycloalkylamine of formula 5.

In Route 2, the known starting tetracycle of formula 10 is reacted with a base such as lithiumdiisopropylamide (LDA) in a suitable solvent such as THF, then with a benzaldehyde of formula 11. The resultant compound of formula 12 is then reduced, for example by hydrogenation with palladium catalyst and hydrogen in the presence of HCl to obtain a compound of formula Ia.

Route 3

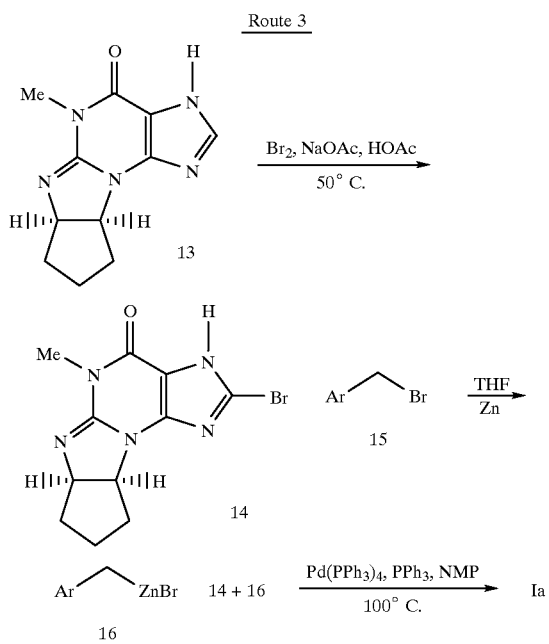

In Route 3, the known starting material of formula 13 is brominated, for example by reaction with a mixture of bromine and sodium acetate in HOAc. The reagent of formula 16 is prepared by treating with zinc a bromomethyl aryl compound of formula 15 (wherein Ar is optionally substituted phenyl or naphthyl). The reagent of formula 16 is then reacted with the compound of formula 14 in the presence of a catalyst such as tetrakis-(triphenylphosphine) palladium (Pd(PPh$_3$)$_4$) and triphenylphosphine (PPh3) in the presence of a polar solvent such as NMP under an inert atmosphere.

Other compounds of formula I can be prepared by the following routes 4–6:

Route 4

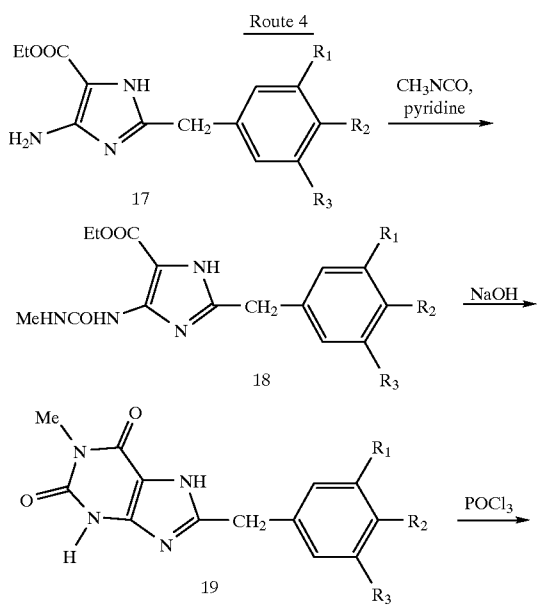

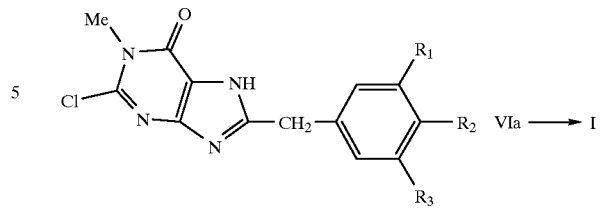

Route 4, wherein R$_1$, R$_2$ and R$_3$ are as defined above, involves reacting a substituted imidazole carboxylate of formula 17 with CH$_3$NCO in the presence of a base such as pyridine. The resultant compound of formula 18 is then heated with an aqueous base such as NaOH to form the bicyclic compound of formula 19, which is then treated with a halide-forming agent such as POCl$_3$ to obtain a compound of formula VIa (i.e., a compound of formula VI wherein R$^4$ is methyl, X is chloro and R$^5$ is optionally substituted benzyl). Compounds of formula VIa are treated as described in the claimed process to obtain compounds of formula I.

Route 5

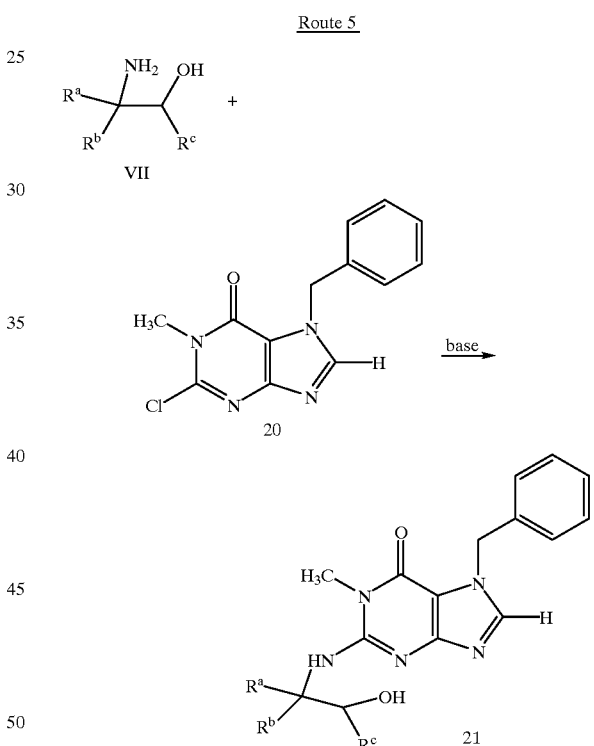

The first step in-Route 5 involves reacting an amino alcohol of formula VII with a chloropurine of formula 20 under the same conditions as step c of the claimed process to obtain a compound of formula 21. Using procedures described in Routes 1 and 2, compounds of formula I can be dehydrated with SOCl$_2$ or triphenylphosphine dibromide to form a polycyclic compound, which is then reacted with a base such as LDA in a dry solvent such as THF at low temperature, treated with an electrophile such as an aryl aldehyde of formula 11 and hydrogenated to give compounds of formula I.

Compounds of formula Ib wherein $R^a$ is hydrogen and $R^b$ and $R^c$ complete a tetrahydrofuran ring are prepared by the following procedure:

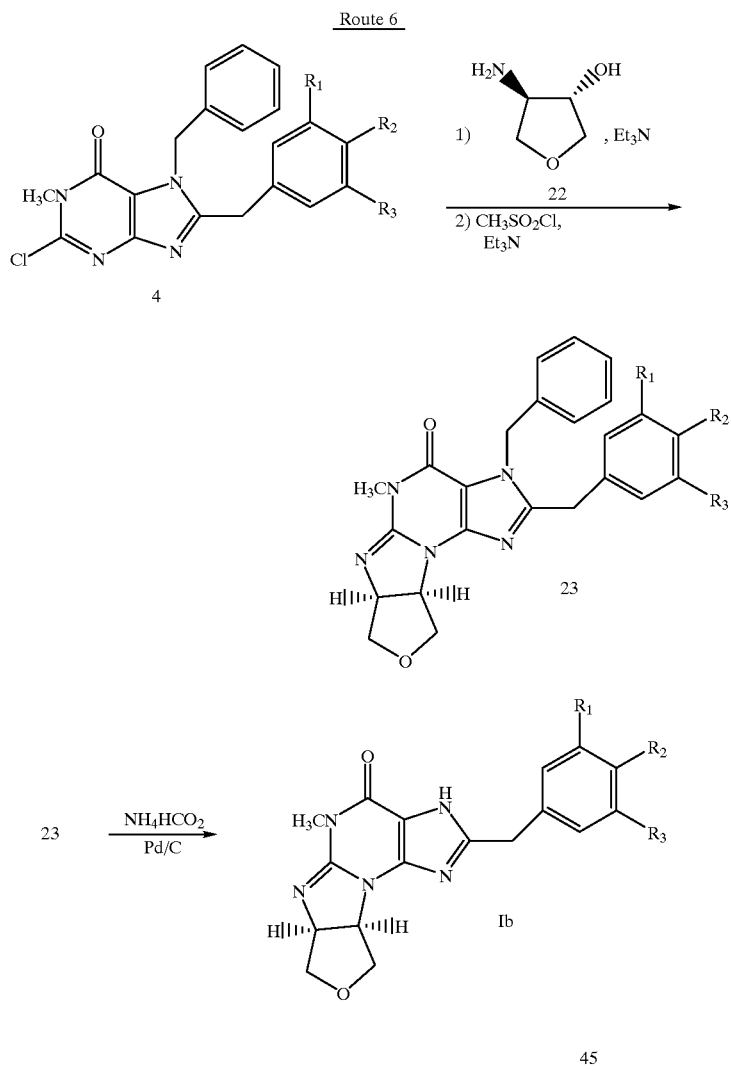

In the above procedure, a chloropurine of formula 4 is reacted at elevated temperature with an amino alcohol of formula 22 in the presence of a base such as $Et_3N$ and in a solvent such as NMP, and the resultant intermediate product is then reacted with $CH_3SO_2Cl$ in the presence of a base such as $Et_3N$ to obtain an intermediate of formula 23. The intermediate of formula 23 is then subjected to hydrogenolysis, for example by treatment with $NH_4HCO_2$ and a palladium catalyst, to obtain a compound of formula Ib.

Intermediate amino alcohols of formula 22 can be prepared by methods known in the art, for example by the following procedure:

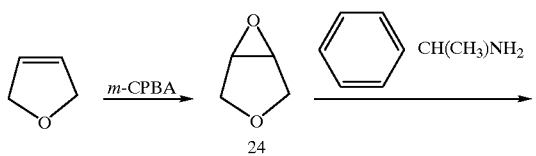

wherein 1,4-dihydrofuran is reacted with m-chloroperoxybenzoic acid (m-CPBA) to obtain the compound of formula 24, which is then reacted with R-(+)-α-methylbenzylamine to give the substituted amino alcohol of formula 25. The diastereomeric intermediates of formula 25 are separated at this stage by recrystallization from $CH_2Cl_2$ and hexane. Compound 25 is then hydrogenated by refluxing with $NH_4HCO_2$ in $CH_3OH$ over Pd/C to give the trans-substituted aminoalcohol of formula 22.

Starting materials of formulae 1, 2, 5, 8, 10, 11, 13, 15 and 17 are readily available or can be prepared by methods well known in the art.

The following examples are presented to illustrate typical intermediate compounds of the present invention, but the scope of the invention is not to be considered limited to such examples. In the formulae, Me is methyl.

PREPARATION 1

N-(6-Amino-1,2,3,4-tetrahydro-3-methyl-2,4-dioxo-5-pyrimidinyl) acetamide

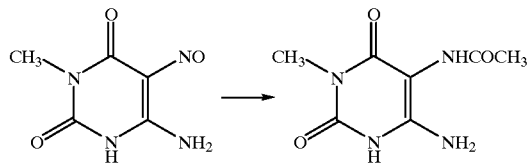

Method 1: Hydrogenate overnight, in a parr shaker, a mixture of 100 g of 6-amino-3-methyl-5-nitroso-2,4(1H, 3H)-pyrimidinedione and 20 g of 5% Pd/C catalyst in 1.0 L of glacial HOAc. Filter the reaction mixture through 10 g of a diatomaceous earth known as celite®, trademark of the Johns-Manville Products Corporation, Celite Division, Manville, N.J. Wash the celite cake with 125 mL of glacial HOAc and save the cake. Add 45 mL of acetic anhydride along with optionally, a trace of DMAP as a catalyst to the filtrate. Stir the mixture overnight at 40° C. and then concentrate to dryness under vacuum. Add 125 mL of water to the resultant solid and stir the mixture at 0° C. in an ice-water bath for 1 hour. Filter the resultant solid and dry in a draft oven at 40–50° C. to obtain 26.3 g of product. Extract the celite cake with eight 250 mL portions of hot HOAc. Concentrate the extracts to obtain a tan solid, slurry in 300 mL water and then treat as described above to give 85.4 g of product. Combining the solids gives 111.7 g (95% crude yield) of the title compound. Recrystallize a sample from hot CH₃OH/HOAc/C to give the purified title compound as a white solid, melting point (m.p.) greater (>) than 250° C. MS (EI): 198 (M+).

Method 2: Hydrogenate overnight, in a parr shaker, a suspension of 1 g of 6-amino-3-methyl-5-nitroso-2,4(1H, 3H)-pyrimidinedione and 0.1 g 5% Pd/C catalyst in 12.2 mL of 1N NaOH. Filter the catalyst, wash with a small amount of 1N NaOH, cool the filtrate to 0° C., stir and add 2 mL of acetic anhydride. Stir for two hours while allowing the reaction mixture to warm to room temperature, filter, wash with water followed by hexanes and dry overnight in a draft oven at 45° C. to obtain 0.82 g (70% yield ) of title compound, a light tan solid.

PREPARATION 2

N-(6-Amino-1,2,3,4-tetrahydro-3-methyl-2,4-dioxo-5-pyrimidinyl) phenylacetamide

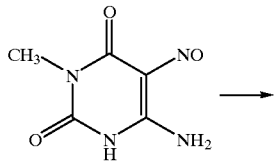

-continued

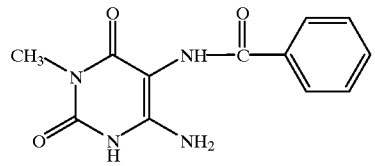

In a parr shaker, hydrogenate overnight a suspension of 1 g of 6-amino-3-methyl-5-nitroso-2,4(1H, 3H)-pyrimidinedione and 0.1 g of 5% Pd/C catalyst in 6.2 mL of 1N NaOH. Filter the catalyst, wash with a small amount of 1N NaOH, cool the filtrate to 0° C., stir and add 0.75 mL of benzoyl chloride. Stir for 1 hr, filter (save the filtrate), wash the product with water followed by hexanes and dry in a draft oven at 45° C. to obtain 1.06 g of product as a light yellow solid. The filtrate is stirred at 0° C. and 0.375 mL benzoyl chloride is added. From this, 0.31 g of product is collected as above, to give 1.36 g (89% total yield) of title compound, MS (Cl/CH₄): 261 (M+H) m.p.>250° C.

PREPARATION 3

N-(4-Amino-1,6 dihydro-2-methoxy-1-methyl-6-oxo-5-pyrimidinyl)acetamide

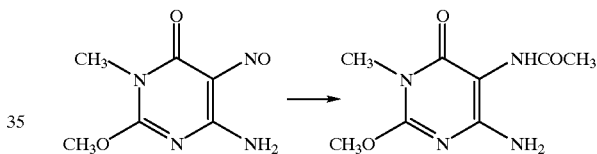

In a parr shaker, hydrogenate overnight a mixture of 4.5 g of 6-amino-2-methoxy-3-methyl-5-nitroso-4(3H)-pyrimidinedione and 0.45 g of 5% Pd/C catalyst in 45 mL of glacial HOAc. Filter the reaction mixture through 1.1 g celite. Wash the celite cake with 1.2 mL glacial HOAc. To the filtrate add 2.8 mL acetic anhydride, and optionally, a trace of DMAP as a catalyst. Stir the mixture 1 hour at room temperature and then filter to collect first crop (0.86 g) of product. Concentrate the mother liquor and filter to collect additional 2.5 g of product. Finally, concentrate the mother liquor to obtain 1.2 g of additional product, to give a total of 4.56 g (90% yield) of the title compound a light tan solid. MS: (FAB) 213 (M+H).

PREPARATION 3.1

N-(6-Amino-1,2,3,4-tetrahydro-3-methyl-2,4-dioxo-5-pyrimidinyl)-4-(trifluoromethyl)benzeneacetamide

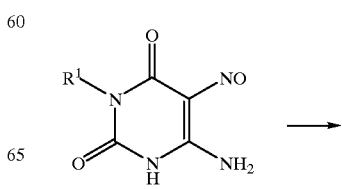

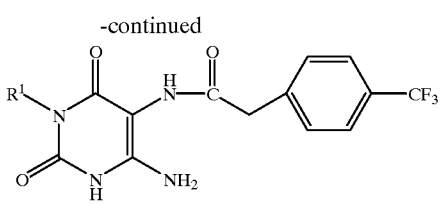

Hydrogenate, in a Parr shaker, a suspension of 2.3 g of 6-amino-3-methyl-5-nitroso-2,4(1H, 3H)-pyrimidinedione and 0.23 g 5% Pd/C in 13 ml 1N NaOH overnight. Filter the catalyst, wash with a small amount of 1N NaOH, cool the filtrate to 0° C., stir and add 4.6 g of p-trifluoromethyl phenyl acetyl chloride. Stir for two hours while allowing it to attain room temperature, filter, wash with water followed by hexanes, and dry overnight in a draft oven (45° C.) to obtain 5.2 g of the title compound, a light tan solid. Suspend this solid in CH2Cl2, stir for 1 h, filter and dry to obtain 4.0 g (87%) of the title compound as an off-white solid, suitable for further reactions, m.p.>300° C. MS (El): 342 (M+), Cl (CH₄): 343 (M+H).

PREPARATION 4

2-Chloro-1,7-dihydro-1,8-dimethyl-6H-purine-6-one

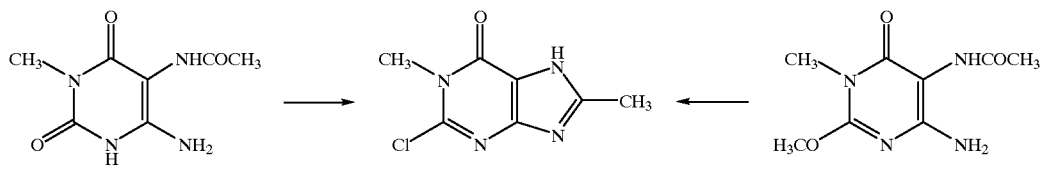

Method 1: Reflux a suspension of 20 g the product of Preparation 1 in 300 mL of POCl₃ for 2–4 days, until the reaction is completed as determined by thin-layer chromatography (TLC). Remove POCl₃ under reduced pressure and add a small amount of ice cold water to the resultant dark gummy solid. Stir this mixture vigorously and then bring to a neutral pH at 0°–5° C. by a slow addition of ice cold NH₄OH. Filter the resultant orange-tan solid, wash with a small amount of ice cold water and dry in a draft oven at 40° C. to give 16.5 g (crude yield 82%) of the title compound. MS (Cl/CH4)199:201 in ~3:1 ratio (M+H), m.p.>250° C.
Method 2: Reflux a mixture of 2 g of the product of Preparation 1 and 0.76 g of NH₄Cl in 30 mL of POCl₃ gently for 1–2 days, until the reaction is completed as determined by TLC. Remove POCl₃ under reduced pressure and add a small amount of ice cold water to the resultant gum. Stir this mixture vigorously and then bring to neutral pH at 0°–5° C. by a slow addition of ice cold NH₄OH. Filter the resultant orange-tan solid, wash with a small amount of ice cold water and dry in a draft oven at 40° C. to give 1.7 g (crude yield 83.5%) of the title compound.
Method 3: Reflux a suspension of 0.55 g the product of Preparation 3 in 12 mL of POCl₃ gently for 2–4 days, until the reaction is completed as determined by TLC. Remove POCl₃ and neutralize as described in Method 1. Filter the resultant light brown solid product and dry in a draft oven at 40° C. to obtain 0.3 g of product. Extract the mother liquor with ethyl acetate, dry the organic layer over anhydrous Na₂SO₄ and concentrate under reduced pressure to obtain 0.05 g of additional product. Finally concentrate the mother liquor to dryness, extract with 10% methanol in ethylacetate (EtOAc), filter and remove the solvents to obtain additional 0.56 g of product, to give a total of 0.41 g (80% yield) of the title compound.

PREPARATION 4.1

2-Chloro-1,7-dihydro-1-methyl-8-[[(4-trifluoromethyl)phenyl]methyl]-6H-purin-6-one

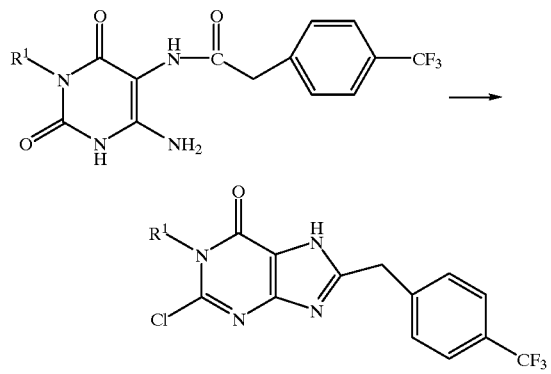

Heat a mixture of 5 g of N-(6-Amino-1,2,3,4-tetrahydro-3-methyl-2,4-dioxo-5-pyrimidinyl)-(4'-trifluoromethyl) phenylacetamide and 1.25 g NH₄Cl in 75 ml POCl₃ at 70° for 24 h (until consumption of the starting material as judged by tlc). Gently reflux (~110° C.) the reaction mixture for 3 days. Remove POCl₃ under reduced pressure. Add a small amount of ice cold CH₂Cl₂ to the resultant gum. Stir this mixture vigorously, then bring to a pH of 9–10 at 0°–5° C. by a slow addition of ice cold NH₄OH. Remove CH₂Cl₂, add a small amount of water (and NH₄OH if needed to maintain neutral to alkaline pH), filter the resultant dark brown solid, wash with a small amount of ice cold water and dry in a draft oven at 40° C. to obtain 5.3 g of the title compound. Slurry this in CH₂Cl₂, filter and dry to obtain 4.6 g (90% mass balance) of the title compound, a light brown solid, suitable for further reactions. MS (Cl/CH₄) 343:345 (M+H) in ~3:1 ratio; El 342:344 (M+) in ~3:1 ratio.

PREPARATION 5

1,7-Dihydro-2-[(2R-hydroxy-R-cyclopentyl)amino]-1,8-dimethyl-6H-purin-6-one

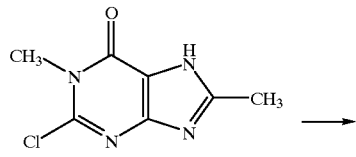

-continued

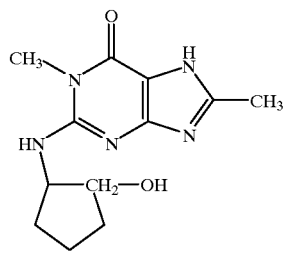

Reflux a mixture of 12.5 g of the product of Preparation 4, 8 g of 2R-hydroxy-R-cyclopentyl amine, and 31.5 mL of Et₃N in 83 mL of CH₃CN for 2–3 days, until the reaction is completed as determined by TLC. Remove the volatiles in the reaction mixture under vacuum and then treat with ice cold water. Stir this suspension at 0–5° C. and filter. Wash the solid with ice cold water and dry in a draft oven at 40° C. to give 14.4 g (crude yield 87%) of the title compound, a light brown solid. m.p. 235–245° C. (decomposition) MS (Cl/CH₄) 264 (M+H); El 263. This compound can be converted to a 2-methyl-polycyclic guanine derivative by employing ring closure procedures described herein or in WO 91/19717.

PREPARATION 5.1

1,7-Dihydro-2-[(2R-hydroxy-R-cyclopentyl)amino]-1-methyl-8-[[(4-(trifluoromethyl) phenyl]methyl]-6H-purin-6-one

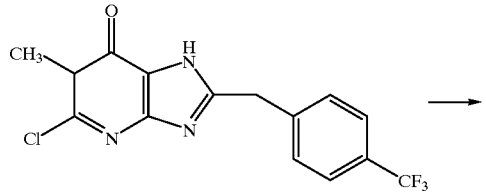

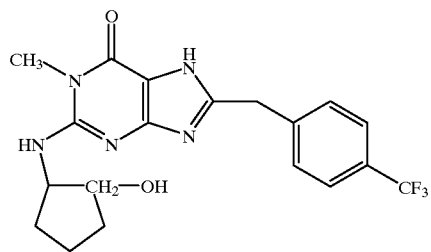

Reflux (~110° C.) a mixture of 90 g of the product of Preparation 4.1, 36.3 g of 2R-hydroxy-R-cyclopentyl amine, and 151 ml iPr₂NEt (Hunig's base) in 151 ml NMP for 24 h (until complete reaction as judged by tlc). Allow to attain room temperature, add 1 L ice cold water, stir vigorously for 1 h and then pour this in 3.5 L water. Stir for 1 8 h, filter and dry in a draft oven at 40° C. to obtain 87 g (81% mass balance) of the title compound, a light tan solid, suitable for further reaction. MS (Cl/CH₄) 408 (M+H); El 407 (M); m.p. 285° C. (decomposition).

The following exemplify preparation of the 2-benzyl-polycylic guanine derivatives.

EXAMPLE 1

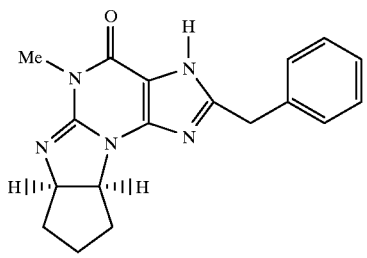

Step 1: Dissolve 6-amino-3-methyl-5-(phenylmethylamino) pyrimidine-2,4-dione (12.3 g), phenylacetic acid (6.80 g), DEC (9.55 g) and DMAP (1.0 g) in dry DMF and stir the reaction mixture overnight at room temperature. Pour the reaction mixture onto ice, filter the product and wash with Et₂O to obtain:

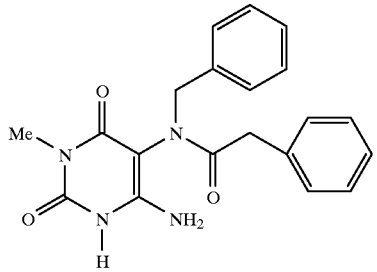

Using appropriate starting materials and essentially the same procedure, the following compounds can also be prepared:

| | | |
|---|---|---|
| 1.1a | 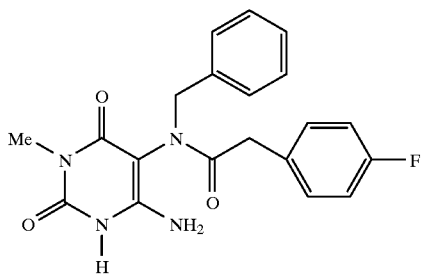 | ¹H NMR(DMSO, 300 MHz)δ 3.00(3H, s, NCH₃), 3.48(2H, bs, COCH₂), 4.55(2H, AB, J$_{A,B}$=14.00Hz, NCH₂), 6.25(2H, bs, NH₂), 7.0–7.50(9H, m, C₆H₅ and C₆H₄) |
| 1.1b | 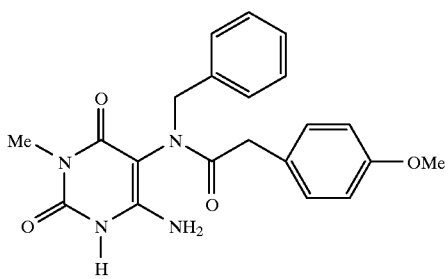 | ¹H NMR(DMSO, 200 MHz)δ 3.00(3H, s, NCH₃), 3.35(2H, bs, COCH₂), 3.70(3H, s, OCH₃), 4.52(2H, AB, J$_{A,B}$=15.00Hz, NCH₂), 6.18(2H, bs, NH₂), 6.8 and 7.05 (4H, 2d, C₆H₄OMe), 7.2–7.40(5H, m, C₆H₅) |
| 1.1c | 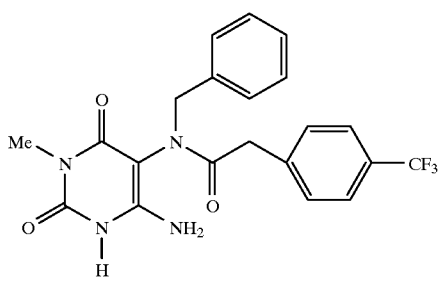 | ¹H NMR(DMSO, 300 MHz)δ 3.00(3H, s, NCH₃), 3.60(2H, bs, COCH₂), 4.55(2H, AB, J$_{A,B}$=15.00Hz, NCH₂), 6.30(2H, bs, NH₂), 7.10–7.50(7H, m, C₆H₅ and C₆H₄CF₃), 7.70(2H, d, C₆H₄CF₃) |
| 1.1d | 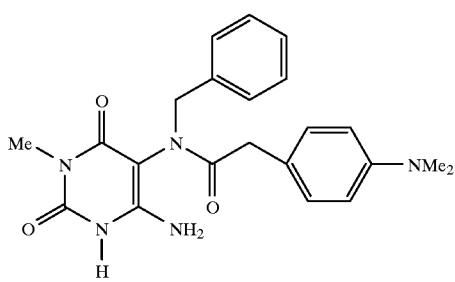 | ¹H NMR(DMSO, 200 MHz)δ 2.88(6H, s, N(CH₃)₂), 3.05(3H, s, NCH₃), 3.35(2H, bs, COCH₂), 4.58(2H, AB, J$_{A,B}$=14.00Hz, NCH₂), 6.18(2H, bs, NH₂), 6.65 and 6.96 (4H, 2d, J=8.65, C₆H₄NMe₂), 7.25(5H, m, C₆H₅) |
| 1.1e | 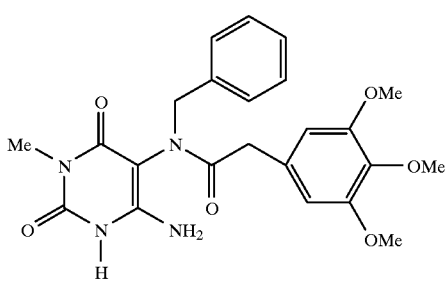 | ¹H NMR(DMSO, 200 MHz)δ 3.15(3H, s, NCH₃), 3.95(2H, bs, COCH₂), 3.60(3H, s, OCH₃), 3.80(6H, s, 2OCH₃), 4.60(2H, AB, J$_{A,B}$=15.00Hz, NCH₂), 6.18(2H, bs, NH₂), 6.50(2H, s C₆H₂(OMe)₃), 7.2–7.50 (5H, m, C₆H₅) |

| | | |
|---|---|---|
| 1.1f | 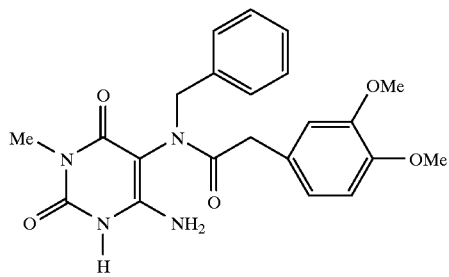 | ¹H NMR(DMSO, 200 MHz)δ 3.10(3H, s, NCH₃), 4.20(2H, bs, COCH₂), 3.70(6H, s, 2OCH₃), 4.50(2H, AB, J_{A,B}=16.00Hz, NCH₂), 6.10(2H, bs, NH₂), 6.80(3H, m C₆H₃(OMe)₂), 7.2–7.50(5H, m, C₆H₅) |

Step 2: Dissolve compound 1.1 (5.0 g) in 150 mL of POCl₃ and reflux for 8 h. Cool the reaction mixture and pour into 300 mL of hexane. Let the reaction mixture stand for 0.5 h. Decant the solvent, cool the remaining residue, adjust to pH 8 with 3 N NaOH, extract with 3×200 mL of CH₂Cl₂, dry and evaporate the solvent. Column chromatograph the residue (2:98 MeOH:CH₂Cl₂) to obtain the product.

| | | |
|---|---|---|
| 1.2 | 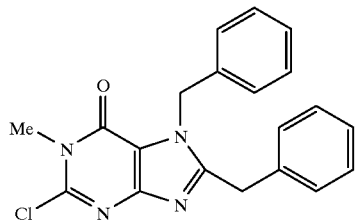 | ¹H NMR(CDCl₃, 200 MHz)δ 3.80(3H, s, NCH₃), 4.30(2H, s, CH₂Ph), 5.50(2H, s, NCH₂Ph), 7.35(10H, m, 2C₆H₅) |

Using appropriate starting materials and essentially the same procedure, following compounds can also be prepared:

| | | |
|---|---|---|
| 1.2a | 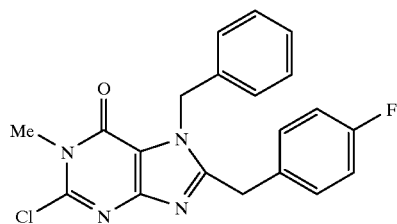 | ¹H NMR(CDCl₃, 200 MHz)δ 3.75(3H, s, NCH₃), 4.10(2H, s, CH₂PhF), 5.50(2H, s, NCH₂), 6.90–7.20 and 7.30(9H, 2m, C₆H₄F and C₆H₅) |
| 1.2b | 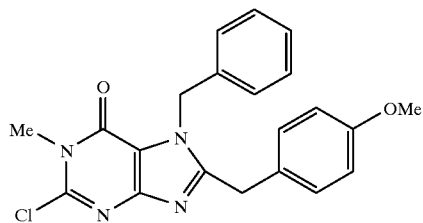 | ¹H NMR(CDCl₃, 200 MHz)δ 3.70(3H, s, NCH₃), 3.80(3H, s, OCH₃), 4.05(2H, s, CH₂PhOMe), 5.50(2H, s, NCH₂Ph), 6.80 (2H, d, J=8.50Hz, C₆H₄OMe), 7.0–7.10 and 7.30(7H, 2m, C₆H₄OMe and C₆H₅) |

| | | |
|---|---|---|
| 1.2c | 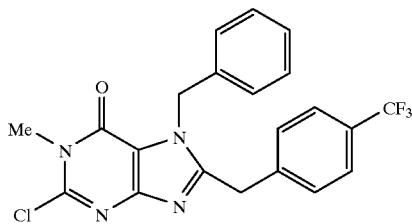 | ¹H NMR(CDCl₃, 200 MHz)δ 3.75(3H, s, NCH₃), 4.18(2H, s, CH₂PhCF₃), 5.55(2H, s, NCH₂Ph), 7.00(2H, m, C₆H₄CF₃), 7.20–7.40(5H, m, C₆H₅), 7.50(2H, d, J=8.20 Hz, C₆H₄CF₃) |
| 1.2d | 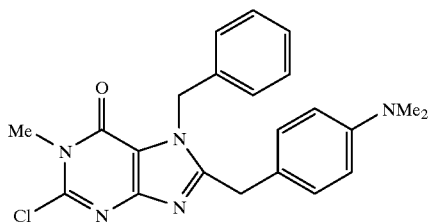 | ¹H NMR(CDCl₃, 200 MHz)δ 2.90(6H, s, N(CH₃)₂), 3.70(3H, s, NCH₃), 4.05(2H, s, CH₂PhNMe₂), 5.45(2H, s, NCH₂Ph), 7.0 (2H, d, C₆H₄NMe₂), 7.0–7.10 and 7.30 (7H, m, C₆H₄NMe₂ and C₆H₅) |
| 1.2e | 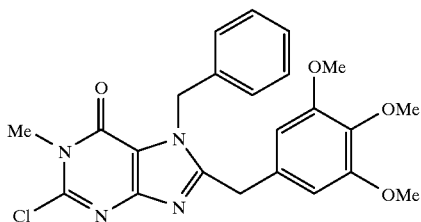 | ¹H NMR(CDCl₃, 200 MHz)δ 3.35(3H, s, NCH₃), 3.60(3H, s, OCH₃), 3.65(6H, s, 2OCH₃), 4.15(2H, s, CH₂Ph(OMe)₃), 5.70 (2H, s, NCH₂Ph), 6.45(2H, s, C₆H₂—(OMe)₃), 7.10 and 7.30(5H, 2m, C₆H₅) |
| 1.2f | 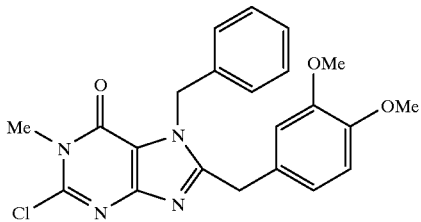 | ¹H NMR(CDCl₃, 200 MHz)δ 3.72(3H, s, NCH₃), 3.78 and 3.85(6H, 2s, 2OCH₃), 4.08(2H, s, CH₂Ph(OMe)₂), 5.50(2H, s, NCH₂Ph), 6.70(3H, m, C₆H₃), 7.05 and 7.30(5H, 2m, C₆H₅) |

45

Suspend compound 1.2 (2.70 g), trans-2-hydroxycyclopentylamine (1.40 g) and i-Pr₂NEt (5.20 mL) in 10 mL of NMP and seal the reaction vessel. Keep the mixture at 120–125° C. for 6–8 h. Cool the reaction mixture, add 20 mL of ice water and filter the precipitate with cold water and dry to obtain the product:

| | | |
|---|---|---|
| 1.3 | 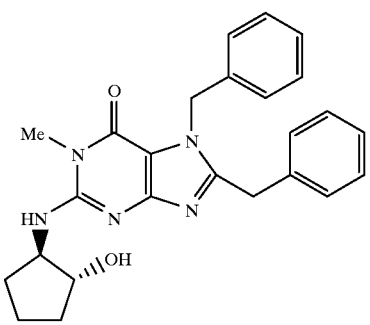 | ¹H NMR(CDCl₃, 200 MHz)δ 1.40–2.20 (6H, m), 3.38(3H, s, NCH₃), 4.00(2H, s, CH₂Ph), 4.10(2H, m), 5.50(2H, AB, J_{A,B}=14.0Hz, NCH₂Ph), 7.20–7.30(10H, m, C₆H₅) |

Using appropriate starting materials and teh same procedure, the following compounds can also be prepared:

1.3a 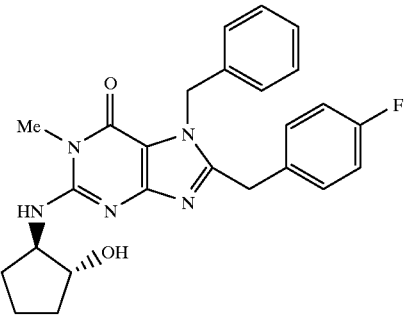

$^1$H NMR(CDCl$_3$, 200 MHz)δ 1.40–2.30 (6H, m), 3.40(3H, s, NCH$_3$), 4.00(2H, s, CH$_2$PhF), 4.10(2H, m), 5.40(2H, AB, J$_{A,B}$=14.0Hz, NCH$_2$Ph), 7.20 and 7.30 (9H, 2m, C$_6$H$_5$ and C$_6$H$_4$F)

1.3b 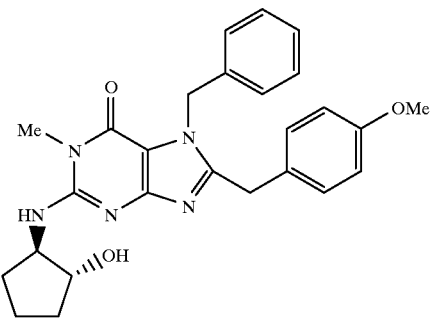

$^1$H NMR(CDCl$_3$, 200 MHz)δ 1.45–2.30 (6H, m), 3.40(3H, s, NCH$_3$), 3.75(3H, s, OCH$_3$), 4.00(2H, s, CH$_2$PhOMe), 4.10 (2H, m), 4.75(1H, d, J=1.80Hz), 5.45(2H, AB, J$_{A,B}$=14.0Hz, NCH$_2$Ph), 6.88 and 7.05(4H, 2d, J=8.0Hz, C$_6$H$_4$OMe), 7.05 and 7.30(5H, 2m, C$_6$H$_5$)

1.3c 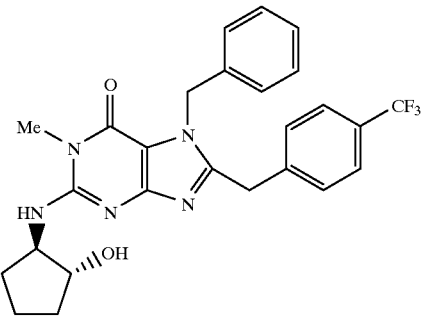

$^1$H NMR(CDCl$_3$, 300 MHz)δ 1.50–2.40 (6H, m), 3.48(3H, s, NCH$_3$), 4.15(2H, s, CH$_2$PhCF$_3$), 4.10(2H, m), 4.68(1H, d, J=1.80Hz), 5.50(2H,AB, J$_{A,B}$=14.0Hz, NCH$_2$Ph), 7.05(2H, dd, J=8.0 and 1.80 Hz, C$_6$H$_4$CF$_3$), 7.27(5H, m, C$_6$H$_5$), 7.51 (2H, d, J=8.0Hz, C$_6$H$_4$CF$_3$)

1.3d 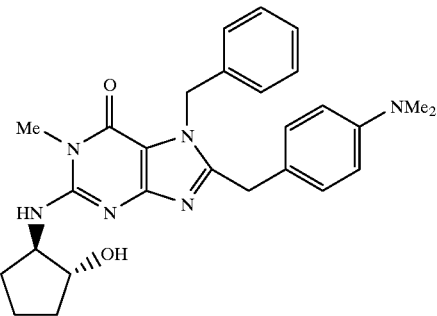

$^1$H NMR(CDCl$_3$, 200 MHz)δ 1.40–2.40 (6H, m), 2.90(6H, s, N(CH$_3$)$_2$), 3.40(3H, s, NCH$_3$), 3.95(2H, s, CH$_2$PhNMe$_2$), 4.05 (2H, m), 4.80(1H, d, J=2.0Hz), 5.45(2H, AB, J$_{A,B}$=15.0Hz, NCH$_2$Ph), 6.65 and 7.05(4H, 2d, J=8.0Hz, C$_6$H$_4$NMe$_2$), 7.10 and 7.30(5H, 2m, C$_6$H$_5$)

| | | |
|---|---|---|
| 1.3e | 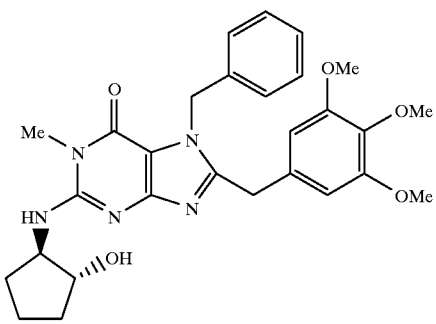 | $^1$H NMR(CDCl$_3$, 200 MHz)δ 1.45–2.20 (6H, m), 3.40(3H, s, NCH$_3$), 3.75(6H, s, 2OCH$_3$), 3.85(3H, s, OCH$_3$), 4.00(2H, s, CH$_2$Ph(OMe)$_3$), 4.10(2H, m), 5.50(2H, AB, J$_{A,B}$=14.50Hz, NCH$_2$Ph), 6.35(2H, s, C$_6$H$_4$(OMe)$_3$), 7.05 and 7.30(5H, 2m, C$_6$H$_5$) |
| 1.3f | 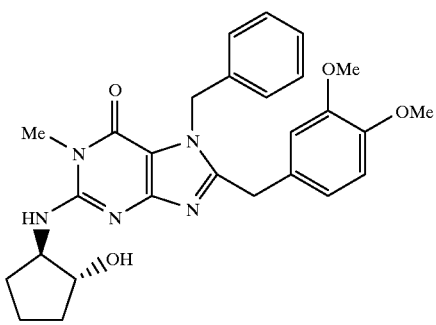 | $^1$H NMR(CDCl$_3$, 200 MHz)δ 1.45–2.30 (6H, m), 3.45(3H, s, NCH$_3$), 3.78 and 3.85 (6H, 2s, 2OCH$_3$), 4.05(2H, s, CH$_2$Ph—(OMe)$_2$), 4.10(2H, m), 5.45(2H, AB, J$_{A,B}$=15.0Hz, NCH$_2$Ph), 6.75(3H, 2d, C$_6$H$_4$(OMe)$_2$), 7.05 and 7.28(5H, 2m, C$_6$H$_5$) |

Step 4: Add 2.30 g of SOCl$_2$ (19.35 mmol) to a solution of compound 1.3 (2.75 g, 6.45 mmol) in CH$_2$Cl$_2$ and stir the reaction mixture overnight. Wash the reaction mixture with cold 2 N NaOH, dry and evaporate the solvent. Chromatograph the residue on silica, eluting with CH$_2$Cl$_2$/CH$_3$OH (98:2) to give the product:

| | | |
|---|---|---|
| 1.4 | 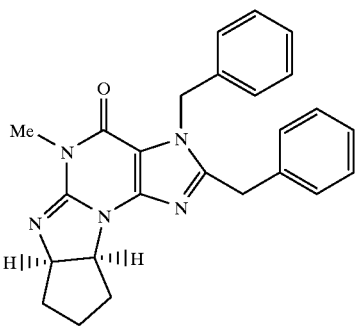 | $^1$H NMR(CDCl$_3$, 200 MHz)δ 1.45–2.05 (5H, m), 2.20(1H, dd), 3.40(3H, s, NCH$_3$), 3.98(2H, s, CH$_2$Ph), 4.75(1H, t) 4.90(1H, t), 5.50(2H, s, NCH$_2$Ph), 7.10 and 7.30 (10H, 2m, C$_6$H$_5$) |

Using appropriate starting materials and essentially the same procedure, the following compounds can also be prepared:

| | | |
|---|---|---|
| 1.4a | 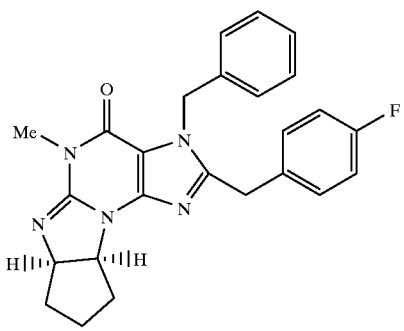 | ¹H NMR(CDCl₃, 200 MHz)δ 1.50–2.10 (5H, m), 2.30(1H, dd), 3.40(3H, s, NCH₃), 4.00(2H, s, CH₂PhF), 4.80(1H, t) 4.92(1H, t), 5.42(2H, s, NCH₂Ph), 7.10 and 7.32(9H, 2m, C₆H₅ and C₆H₄F) |
| 1.4b | 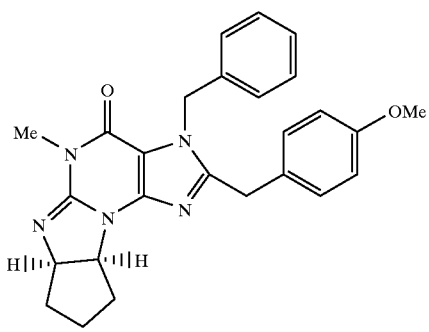 | ¹H NMR(CDCl₃, 200 MHz)δ 1.50–2.00 (5H, m), 2.28(1H, dd), 3.35(3H, s, NCH₃), 3.80(3H, s, OCH₃), 3.98(2H, s, CH₂PhOMe), 4.75(1H, t) 4.85(1H, t), 5.35(2H, s, NCH₂Ph), 6.80 and 7.05 (4H, 2d, J=8.0Hz, C₆H₄OMe), 7.10 and 7.30(5H, 2m, C₆H₅) |
| 1.4c | 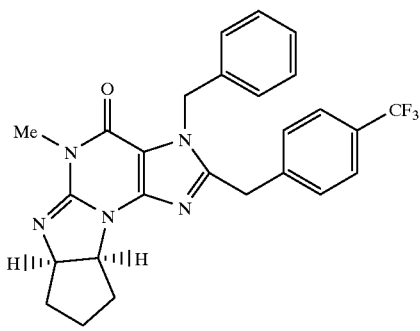 | ¹H NMR(CDCl₃, 200 MHz)δ 1.50–2.10 (5H, m), 2.28(1H, dd), 3.38(3H, s, NCH₃), 4.08(2H, s, CH₂PhCF₃), 4.78 (1H, t), 4.90(1H, t), 5.40(2H, s, NCH₂Ph), 7.05(2H, dd, J=8.0 and 1.80 Hz, C₆H₅), 7.30(3H, m, C₆H₅), 7.20 and 7.50(4H, 2d, J=8.0Hz, C₆H₄CF₃) |
| 1.4d | 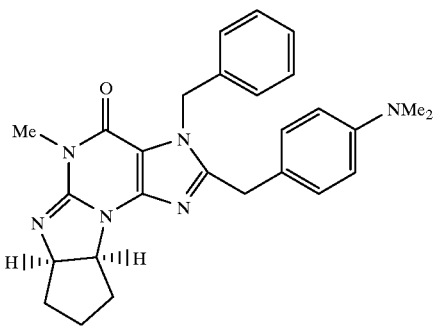 | ¹H NMR(CDCl₃, 200 MHz)δ 1.50–2.00 (5H, m), 2.30(1H, dd), 2.90(6H, s, N(CH₃)₂), 3.30(3H, s, NCH₃), 3.92(2H, CH₂PhNMe₂), 4.72(1H, t), 4.88(1H, t), 5.35(2H, s, NCH₂Ph), 6.65 and 7.00 (4H, 2d, J=8.0Hz, C₆H₄NMe₂), 7.12 and 7.30(5H, 2m, C₆H₅) |

| | |
|---|---|
| 1.4e 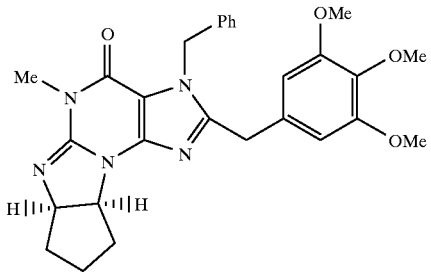 | ¹H NMR(CDCl₃, 200 MHz)δ 1.50–2.00 (5H, m), 2.25(1H, dd), 3.35(3H, s, NCH₃), 3.70(6H, s, 2OCH₃), 3.80(3H, s, OCH₃), 3.95(2H, s, CH₂Ph(OMe)3), 4.75 (1H, t) 4.90(1H, t), 5.40(2H, s, NCH₂Ph), 6.30(2H, s, C₆H₄(OMe)₃), 7.10 and 7.30 (5H, 2m, C₆H₅) |
| 1.4f 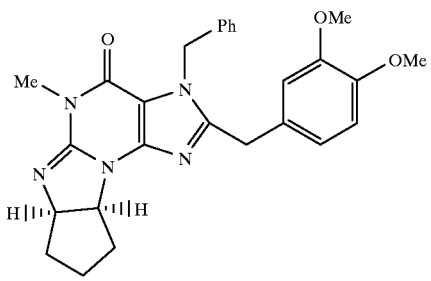 | ¹H NMR(CDCl₃, 200 MHz)δ 1.50–2.00 (5H, m), 2.40(1H, dd), 3.40(3H, s, NCH₃), 3.78(6H.s. 2OCH₃), 3.85(3H, s, OCH₃), 4.10(2H, s, CH₂Ph(OMe)₂), 4.75 (1H, t) 4.85(1H, t), 5.50(2H, s, NCH₂Ph), 6.80 and 6.62(3H, 2m, C₆H₄(OMe)₂), 7.10 and 7.30(5H, 2m, C₆H₅) |

Step 5: Suspend compound 1.4 (4.00 g) and 10% Pd/C (4.00 g) in 100 mL of CH₃OH, add NH₄HCO₂ and reflux for 6 h. Cool the reaction mixture, filter and evaporate the solvent. Add 20 mL of water to the resultant residue, adjust to pH to 8, extract with CH₂Cl₂, dry and evaporate the solvent to produce the title compound (1): ¹H NMR (CDCl₃+drop of CD₃OD, 200 MHz) δ 1.50 (1 H, m), 1.65–2.00(5 H, m),2.28 (1 H, J=7.50 & 12.50 Hz), 3.28 (3 H, s, NCH₃), 4.18 (2 H, s, CH₂Ph), 4.75(1 H, t, J=7.00 Hz), 4.90 (1 H, t, J=7.00 Hz), 7.30 (5 H, m, C₆C₅).

Using the same procedure, hydrogenate compounds 1.4a to 1.4c of Step 4 to obtain the following compounds:

| | |
|---|---|
| 1A 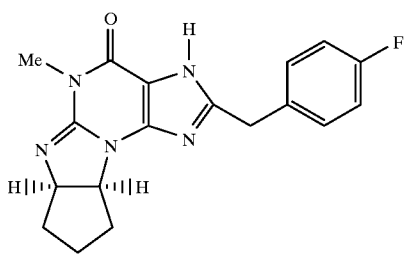 | ¹H NMR(CDCl₃+drop of CD₃OD, 200 MHz)δ 1.50–2.00(5H, m), 2.25(1H, dd, J=13.00 and 5.00Hz), 3.38(3H, s, NCH₃), 4.15(2H, s, CH₂C₆H₄F), 4.72(1H, t, J=7.00Hz), 4.85(1H, t, J=7.00Hz), 6.95 and 7.30(4H, 2d, J=10Hz, C₆H₄F) |
| 1B 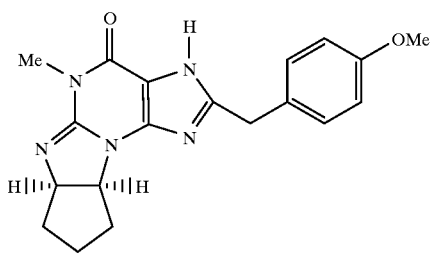 | ¹H NMR(CDCl₃+drop of CD₃OD, 300 MHz)δ 1.50–2.00(5H, m), 2.28(1H, dd, J=13.50 and 5.20Hz), 3.38(3H, s, NCH₃), 3.50(3H, s, OCH₃), 4.10(2H, s, CH₂C₆H₄OMe), 4.72(1H, t, J=7.00Hz), 4.88(1H, t, J=7.00Hz), 6.85 and 7.25(4H, 2d, J=10.0Hz, C₆H₄OMe) |

| | |
|---|---|
| 1C 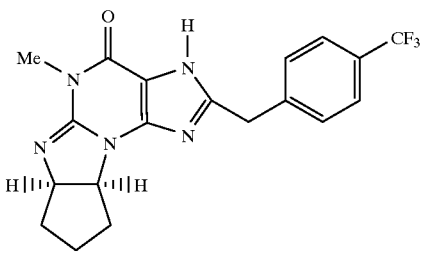 | ¹H NMR(CDCl₃+drop of CD₃OD, 300 MHz)δ 1.50–2.00(5H, m), 2.25(1H, dd, J=13.50 and 5.20Hz), 3.35(3H, s, NCH₃), 4.22(2H, s, CH₂C₆H₄CF₃), 4.72(1H, t, J=7.00Hz), 4.88(1H, t, J=7.00Hz), 7.48 and 7.58(4H, 2d, J=8.0Hz, C₆H₄CF₃) |

EXAMPLE 2

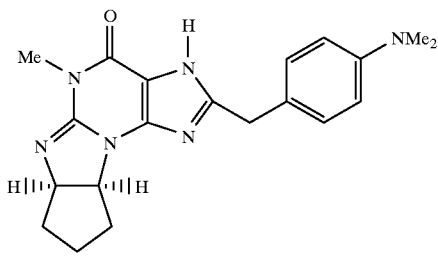

Dissolve compound 1.4d (2.0 g) in 100 mL of absolute EtOH, add 5 mL of EtOH saturated with HCl gas and 20% Pd(OH)₂ (2.0 g). Hydrogenate the reaction mixture at 60 psi for 24 h. Basify the reaction with NH₄OH, filter and evaporate the solvent. Redissolve the residue in CH₂Cl₂, wash with water, dry and evaporate the solvent. Column chromatograph the residue (95:5 CH₂Cl₂:MeOH) to obtain the title compound: ¹H NMR (CDCl₃+drop of CD₃OD, 300 MHz) δ 1.50–2.00 (5 H, m), 2.25 (1 H, dd, J=13.50 and 5.20 Hz), 2.95 (6 H, t, J=7.00 Hz), 4.88 (1 H, t, J=7.00 Hz), 6.70 and 7.15 (4 H, 2 d, J=8.0 Hz, C₆H₄NMe₂).

Using the same procedure, treat the compounds 1.4e and 1.4f to obtain compounds 2A and 2B, respectively:

| | |
|---|---|
| 2A 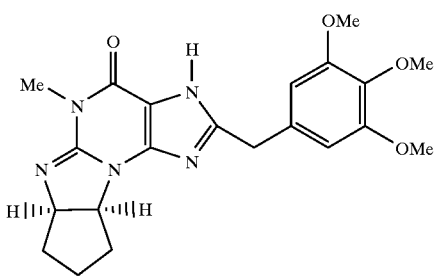 | ¹H NMR(CDCl₃+drop of CD₃OD, 300 MHz)δ 1.50–2.00(5H, m), 2.25(1H, dd, J=13.50 and 5.20Hz), 3.40(3H, s, NCH₃), 3.85(9H, s, 3OCH₃), 4.10(2H, s, CH₂C₆H₄OMe), 4.72(1H, t, J=7.00Hz), 4.88(1H, t, J=7.00Hz), 6.50(2H, s, C₆H₂(OMe)₃) |
| 2B 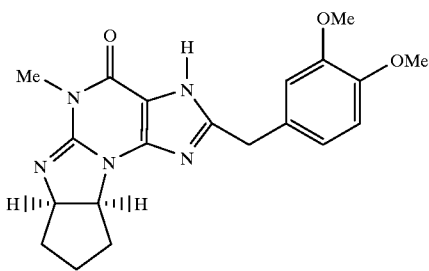 | ¹H NMR(CDCl₃+drop of CD₃OD, 200 MHz)δ 1.50–2.00(5H, m), 2.25(1H, dd, J=13.00 and 5.20Hz), 3.35(3H, s, NCH₃), 3.85 and 3.88(6H, 2s, 2OCH₃), 4.10(2H, s, CH₂C₆H₄(OMe)₂), 4.75(1H, t, J=7.00 Hz), 4.85(1H, t, J=7.00Hz), 6.85(3H, m C₆H₃(OMe)₂) |

EXAMPLE 3

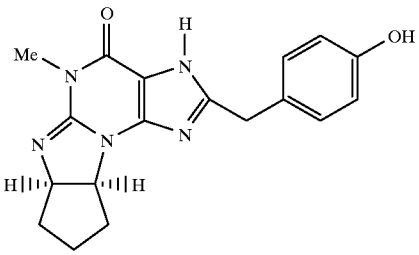

Generate LDA (1.2 mmol) in THF (15 mL and cool to −78° C. Add a THF solution of(+)-cis-5,6a,7,8,9,9a-hexahydro-5-methyl-3-(phenylmethyl)-cyclopent[4,5]imidazo[2,1-b] purin-4-one (1.0 mmol) and stir the reaction for 0.5 h at −78° C. Add a solution of 4-benzyloxybenzaldehyde (1.0 mmol) in THF, slowly warm the reaction mixture to −40° C. and stir for 0.5 h at −40° C. Quench the reaction with a saturated NH$_4$Cl solution and evaporate the solvent. Proceed as described in Example 2 to obtain the title compound: $^1$H NMR (CDCl$_3$+drop of CD$_3$OD, 300 MHz) δ 1.60 (1 H, m), 1.70–2.00 (4 H, m), 2.20 (1 H, dd, J=10.00 dn 4.00 Hz), 3.30 (3 H, s, NCH$_3$), 4.20 (2 H, s, CH$_2$C$_6$H$_4$OH), 4.72 (1 H, t, J=7.00 Hz), 6.75 and 7.12 (4 H, 2 d, J=8.0 Hz, C$_6$H$_4$OH).

Using appropriate starting materials and essentially the same procedure, the following compounds can also be prepared:

| | | |
|---|---|---|
| 3A | 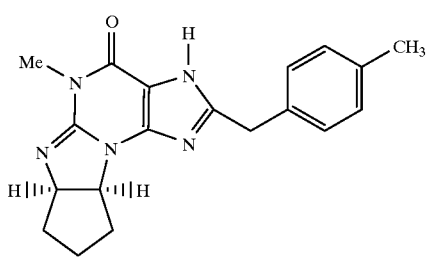 | $^1$H NMR(CDCl$_3$+drop of CD$_3$OD, 200 MHz)δ 1.60–2.00(5H, m), 2.28(1H, dd, J=10.00 and 5.00Hz), 2.32(3H, s, C$_6$H$_4$CH$_3$), 3.35(3H, s, NCH$_3$), 4.12(2H, s, CH$_2$C$_6$H$_4$Me), 4.72(1H, t, J=7.00Hz), 4.88(1H, t, J=7.00Hz), 7.10 and 7.20(4H, 2d, J=8.0Hz, C$_6$H$_4$CH$_3$) |
| 3B | 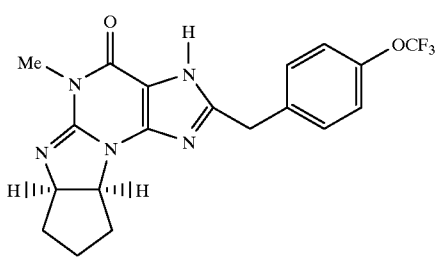 | $^1$H NMR(CDCl$_3$+drop of CD$_3$OD, 200 MHz)δ 1.50–2.00(5H, m), 2.28(1H, dd, J=10.00 and 5.00Hz), 3.35(3H, s, NCH$_3$), 4.18(2H, s, CH$_2$C$_6$H$_4$OCF$_3$), 4.72(1H, t, J=7.00Hz), 4.88(1H, t, J=7.00Hz), 7.15 and 7.40(4H, 2d, J=8.0Hz, C$_6$H$_4$OCF$_3$) |
| 3C | 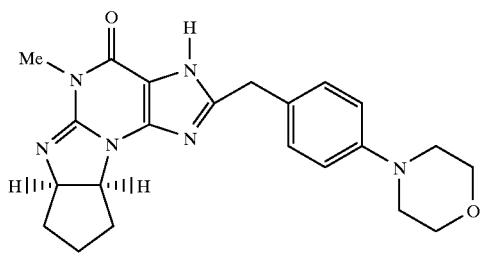 | $^1$H-NMR(300 MHz, CDCl$_3$)δ 1.47–2.31 (m, 6H), 3.05–3.15(m, 4H), 3.38(s, 3H), 3.78–3.86(m, 4H), 4.08(s, 2H), 4.73(t, 1H, J=7Hz), 4.88(t, 1H, J=7Hz), 6.84(d, 2H, J=6.7Hz), 7.24(d, 2H, J=6.8Hz); [α]$_D^{25}$ = +79° (c 0.7, EtOH); |
| 3D | 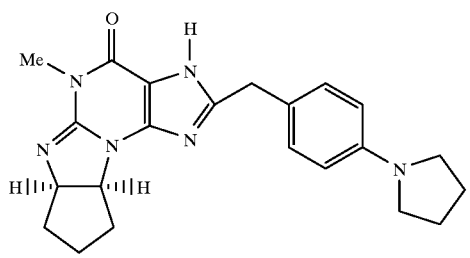 | $^1$H-NMR(200 MHz, CDCl$_3$)δ 1.57–2.35 (m, 10H), 3.21–3.29(m, 4H), 3.40(s, 3H), 4.05(s, 2H), 4.75(t, 1H, J=6.9Hz), 4.91(t, 1H, J=7.0Hz), 6.50(d, 2H, J=8.4Hz), 7.14 (d, 2H, J=8.4Hz); Cl MS 391(M+1, 100%) |

-continued

| | | |
|---|---|---|
| 3E | 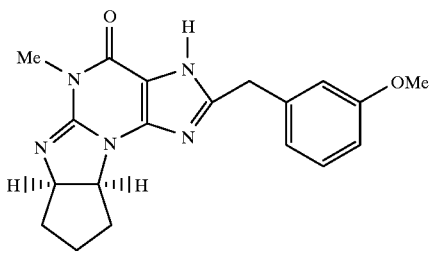 | $[\alpha]_D^{22.5}$ = +134.3° (EtOH) |
| 3F | 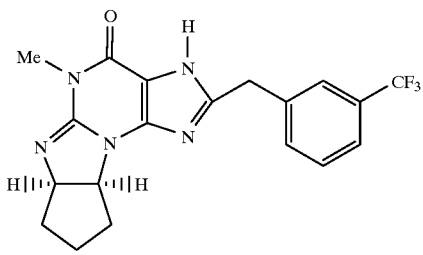 | mp=259–260° C.;<br>FAB MS 390(m+H, 100%) |
| 3G | 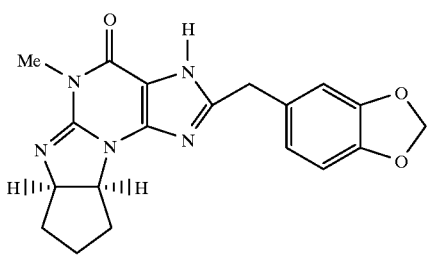 | $[\alpha]_D^{22.5}$ = +108.4° (EtOH) |
| 3H | 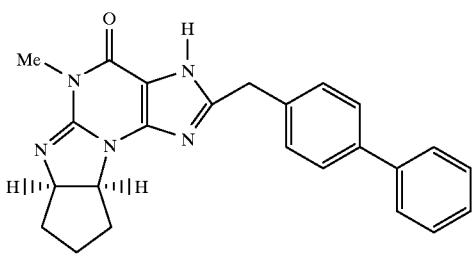 | FAB MS 398(m+H, 100%) |

EXAMPLE 4

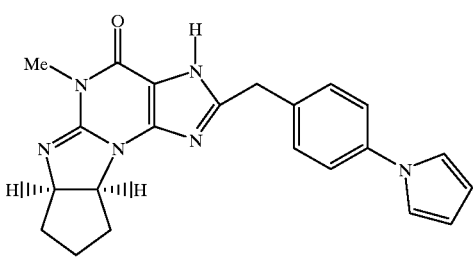

Step 1: React (+)-cis-5,6a,7,8,9,9a-hexahydro-5-methyl-3-(phenylmethyl)-cyclopent[4,5]imidazo[2,1-b]purin-4-one with LDA, then with 4-(1H-pyrrol-1-yl)benzaldehyde in a manner similar to that described in Example 3.

Step 2: Add sodium pellets (24 mg, 1.0 mmol) to a solution of the product of Step 1 (54 mg, 0.11 mmol) in anhydrous THF (15 mL) and liquid ammonia (35 mL) at −78° C. Stir the mixture for 5 min at −78° C., then add solid NH$_4$Cl to quench the reacton. Allow the liquid ammonia to evaporate at room temperature. Triturate the residue with CH$_2$Cl$_2$/CH$_3$OH (9:1), filter, dry over MgSO$_4$ and concentrate. Chromatograph the residue, eluting with CHCl$_3$/MeOH (95:5) to obtain 9.8 mg (23%) of the title compound. Cl MS 387 (M+1, 100%); $^1$H-NMR (300 MHz, CDCl$_3$) d 1.50–2.67 (m, 6H), 3.36 (s, 3H), 4.15 (s, 2H), 4.70 (t, 1H, J=6 Hz), 4.87 (t, 1H, J=8 Hz), 6.28–6.30 (m, 2H), 7.00–7.02 (m, 2H), 7.23–7.38 (m, 4H)

EXAMPLE 5

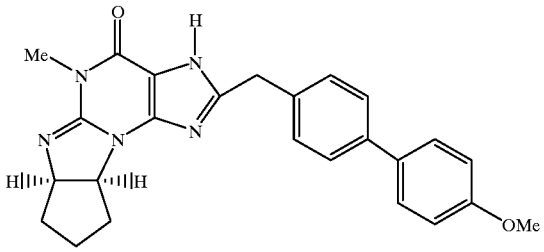

Step 1: Heat a mixture of the compound of Example 1.4b (4.40 g) and pyridine hydrochloride (5.8 g) to 170° C. for 4.5 h. Cool to room temperature, add an ice cold solution of saturated NaHCO$_3$, extract with CH$_2$Cl$_2$, wash the organic layers with brine, dry over MgSO$_4$, filter and concentrate to yield a solid, FAB MS 428 (M+H).

Step 2: Suspend a portion of the product of Step 1 (0.62 9) in DMF (80 mL), cool to 0° C., add N-phenyl trifluoromethane sulfonimde (0.57 g) and K$_2$CO$_3$ (0.39 g). Allow the reaction to warm to room temperature overnight, then pour the reaction mixture into ice water (0.7 L), extract with EtOAc, wash the organic layer with brine, dry over MgSO$_4$, filter and concentrate to dryness.

Step 3: Dissolve a portion of the residue of Step 2 (0.52 g) in dioxane (13 mL), add 4-methoxyphenyltrimethyltin (0.5 g) (prepared from reaction of 4-bromoanisole with t-butyl lithium and trimethyltin chloride), LiCl (0.125 g), Pd(PPh$_3$)$_4$ (0.04 g), and a catalytic amount of BHT. Heat the reaction mixture to reflux for 15 h under a nitrogen atmosphere, cool to room temperature, basify with 10% NH$_4$OH, and extract with EtOAc. Wash the organic layer with brine, dry over MgSO$_4$, filter and concentrate to dryness. Chromatograph the residue on silica gel using CH$_2$Cl$_2$/CH$_3$OH (90:10) to give a light yellow solid, El MS (70 ev) 517 (m+, 100%).

Step 4: Dissolve the solid from Step 3 (0.36 g) in CH$_3$OH (50 mL), add NH$_4$HCO$_2$ (0.66 g) and 10% Pd/C (0.3 g ). Heat this mixture to reflux for 43 h, then add more NH$_4$HCO$_2$ (0.66 g) and continue heating for 8 h, cool to room temperature, filter through celite, concentrate to dryness and partition the residue between 10% NaHCO$_3$ and CH$_2$Cl$_2$. Dry the organic layers over MgSO$_4$, concentrate to dryness and chromatograph the residue on silica gel using CH$_2$Cl$_2$/EtOH/NH$_4$OH (90:10:1) to give the title compound as a colorless solid: $[\alpha]_D^{21}$=+113.9° (MeOH); EV MS (70 ev) 427 (m+, 60%), 398 (100%).

EXAMPLE 6

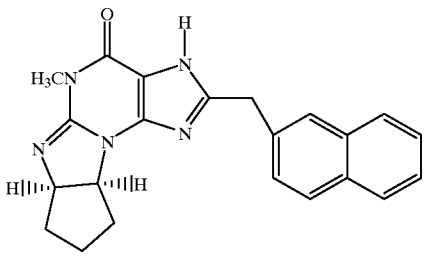

Step 1: To a solution of cis-5,6a,7,8,9,9a-hexahydro-5-methylcyclopenta-[4,5]-imidazo[2,1-b]purin-4(3H)-one (3.38 g, 14.6 mmol) and NaOAc (1.44 g, 17.5 mmol) in HOAc (70 mL) at room temperature and under N$_2$, add bromine (0.91 mL, 17.5 mmol). Stir at 50° C. for 16 h, filter the solids, wash with CHCl$_3$ and air dry to obtain the 2-bromo derivative as a white solid (3.75 g, 83%). $^1$H-NMR (400 MHz, DMSO-d$_6$) δ 1.68–2.24 (m, 6H), 3.32 (s, 3H), 4.81 (t, 1H, J=7 Hz), 5.19 (t, 1H, J=7 Hz), 10.18 (br s,1H); Cl MS 232 (100%), 310 (27%), 312 (25%); $[\alpha]_D^{19.8}$=+100.6° (c 0.63, CH$_3$OH)

Step 2: To a solution of zinc dust (1.70 g, 26 mmol) in dry THF at room temperature, under N$_2$, add 1,2-dibromoethane (0.086 mL, 1.0 mmol) and stir at 65° C. for 1 min. At 0° C., add, dropwise, a solution of 2-bromomethylnaphthalene (4.75 g, 21.5 mmol) in dry THF (11 mL) and stir at 0° C. for 1 h, then at room temperature for 1 h. Heat a portion of the supernatant (3.3 mL, approx. 5.4 mmol) with the product of Step 1 (0.166 g, 0.535 mmol), Pd(PPh$_3$)$_4$ (0.062 g, 0.0544 mmol) and PPh$_3$ (0.028 g, 0.11 mmol) in NMP (2 mL) at 100° C. under argon for 20 h. Evaporate the solvent, dissolve the resultant residue in CHCl$_3$—CH$_3$OH (9-1), wash with sat'd NaHCO$_3$, dry over MgSO$_4$ and concentrate. Separate by flash chromatography, eluting with CHCl$_3$—CH$_3$OH (97-3) to obtain the title compound (0.079 g, 40%). $^1$H-NMR (400 MHz, CDCl$_3$) δ 1.47–2.28 (m, 6H), 3.30 (s, 3H), 4.27–4.35 (AB q, 2H), 4.68 (t, 1H, J=7 Hz), 4.81 (t, 1H, J=7 Hz), 7.40–7.80 (m, 7H); Cl MS 372 (M+1, 100%); $[\alpha]_D^{21.7}$=+78.5° (c 0.41, CHCl$_3$).

EXAMPLE 7

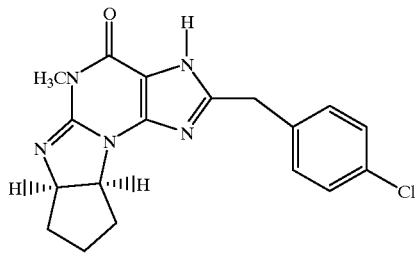

In a manner similar to that of Example 6, using appropriate starting materials, prepare the title compound: $^1$H-NMR (400 MHz, CDCl$_3$) δ 1.49–2.28 (m, 6H), 3.36 (s, 3H), 4.13 (s, 2H), 4.73 (t, 1H, J=7 Hz), 4.87 (t, 1H, J=7 Hz), 7.26–7.27 (m, 4H); Cl MS 356 (100%), 358 (33%); $[\alpha]_D^{21.8}$=+101.0° (c 0.41, CHCl$_3$).

EXAMPLE 8

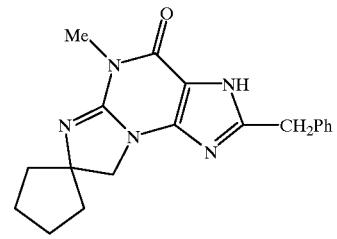

Step 1: Reflux a solution of ethyl 2-benzyl-4-amino-5-imidazole carboxylate (0.89 g, 3.63 mmol) and CH$_3$NCO (8 mL) in pyridine (15 mL) for 2 h. Cool the reaction mixture, evaporate the solvent, extract the residue with EtOAc, wash with water, dry and evaporate. Column chromatograph the residue, eluting with 2% MeOH in CH$_2$Cl$_2$. TLC R$_f$=0.3 (5% MeOH in CH$_2$Cl$_2$); MS 303 (M+1); $^1$H NMR (CDCl$_3$, 200 MHz) δ 1.32 (3H, t, CH$_3$CH$_2$O), 2.90 (3H, d, NHCH$_3$), 4.05 (2H, s, CH$_2$Ph), 4.30 (2H, q, OCH$_2$Me), 7.35 (5H, m, C$_6$H$_5$).

Step 2: Reflux the solution of the product of Step 1 (0.85 g) in 10% (by weight) NaOH (15 mL) for 0.5 h. Cool the reaction mixture, adjust the reaction mixture to pH6 with HOAc and filter. Dry the solid at high vacuum overnight. $^1$H NM (DMSO, 200 MHz) δ 3.15 (3H, s, NCH$_3$), 3.95 (2H, s, CH$_2$Ph), 7.28 (5H, m, C$_6$H$_5$).

Step 3: Reflux a solution of the product of Step 2 (0.84 g) in POCl$_3$ (30 mL) for 24 h. Cool the reaction mixture, pour into hexane (100 mL) and let stand at room temperature for 0.5 h. Decant the solvent, treat the resulting gum with ice cold water, neutralize it with 2N NaOH, extract with CH$_2$Cl$_2$ (2×100 mL), dry and evaporate the solvent. Column chromatograph the residue, eluting with 5% MeOH in CH$_2$Cl$_2$. TLC R$_f$=0.45 (5% MeOH in CH$_2$Cl$_2$); $^1$H NMR (CDCl$_{3, 200}$ MHz) δ 3.80 (3H, s, NCH$_3$), 4.30 (2H, s, CH$_2$Ph), 7.35 (5H, m, C$_6$H$_5$).

Step 4: Suspend the product of Step 3 (0.2 g, 0.73 mmol), 1-amino-1-cyclopentane methanol (0.17 g, 1.45 mmol) and (i-Pr$_2$NEt) (0.25 mL, 1.45 mmol) in NMP (2 mL) and keep the reaction mixture at 130° C. for 6 h. Pour the reaction mixture on ice/water to precipitate the product. Filter the product and dry it under high vacuum. TLC R$_f$=0.28 (5% CH$_3$OH in CH$_2$Cl$_2$); MS 354 (M+1) Fab; $^1$H NMR (CDCl$_3$ + drop of CD$_3$OD, 200 MHz) δ 1.60–2.00 (8H, m), 3.45 (3H, s, NCH$_3$), 3.80 (2H, s, CH$_2$OH), 4.26 (2H, s, CH$_2$Ph), 7.32 (5H, m, C$_6$H$_5$).

Step 5: Treat a suspension of the product of Step 4 (0.08 g, 0.22 mmol) in CH$_2$Cl$_2$ (10 mL) with SOCl$_2$ (0.05 mL) at room temperature overnight. Dilute the reaction mixture with CH$_2$Cl$_2$, wash with cold 1N NaOH, dry and evaporate. Column chromatograph the crude title compound, eluting with 5% MeOH in CH$_2$Cl$_2$ to obtain the title compound. MS 336 (M+1); $^1$H NMR (CDCl$_3$ + drop of CD$_3$OD, 200 MHz) δ 1.60–2.00 (8H, m), 3.56 (3H, s, NCH$_3$), 4.18 (2H, bs, CH$_2$), 4.22 (2H, s, CH$_2$Ph), 7.30 (5H, m, C$_6$H$_5$).

EXAMPLE 9

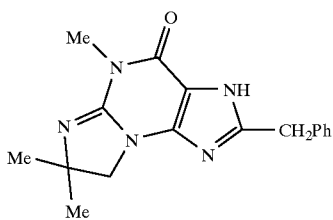

Step 1: Treat a solution of the product of Step 3 of Ex. 8 (0.16 g, 0.58 mmol) and 2-amino-2-methyl propanol (0.13 g, 1.45 mmol) according to procedure described in Step 4 of Ex. 8: MS 328 (M+1) FAB; $^1$H NMR (CDCl$_3$ + drop of CD$_3$OD, 200 MHz) δ 1.45 (6H, s, (CH$_3$)$_2$C), 3.45 (3H, s, NCH$_3$), 3.75 (2H, s, CH$_2$OH), 4.20 (2H, s, CH$_2$Ph), 7.30 (5H, m, C$_6$H$_5$).

Step 2: Treat the product of Step 1 according to the procedure of Step 5 in Ex. 8 to produce the crude title compound. Column chromatograph the crude product, eluting with 7% CH$_3$OH in CH$_2$Cl$_2$ to obtain the title compound. TLC R$_f$=0.60 (7% CH$_3$OH— in CH$_2$Cl$_2$); MS 310 (M+1); $^1$H NMR (CDCl$_3$ + drop of CD$_3$OD, 200 MHz) δ 1.45 (6H, S, (CH$_3$)$_2$C), 3.40 (3H, s, NCH$_3$), 3.90 (2H, s, CH$_2$), 4.16 (2H, s, CH$_2$Ph), 7.35 (5H, m, C$_6$H$_5$).

EXAMPLE 10

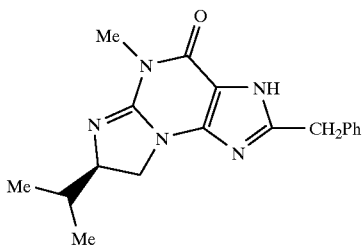

Step 1: Treat the product of Ex. 8, Step 3 (0.20 g, 0.73 mmol) and (R)-2-amino-3-methyl-1-butanol (0.15 g, 1.45 mmol) using the procedure of Ex. 8, Step 4: MS 341; TLC R$_f$=0.40 (10% MeOH in CH$_2$Cl$_2$); $^1$H NMR (CDCl$_3$ + drop of CD$_3$OD, 200 MHz) δ 0.96 and 0.98 (6H, 2d, (CH$_3$)$_2$CH), 2.00 (1H, dt, CH(Me)$_2$), 3.45 (3H, s, NCH$_3$), 3.65 and 3.75 (2H, 2dd, J=15.00 and 6.5 Hz, CH$_2$OH), 4.12 (2H, s, CH$_2$Ph), 7.28 (5H, m, C$_6$H$_5$).

Step 2: Treat the product of Step 1 (0.11 g, 0.32 mmol) with SOCl$_2$ (0.14 g, 0.08 mL) as described in Step 5 of Ex. 8. Column chromatograph the crude product, eluting with 7% CH$_3$OH—CH$_2$Cl$_2$ to obtain the title compound. TLC R$_f$=0.45 (10% CH$_3$OH in CH$_2$Cl$_2$); MS 324 (M+1); $^1$H NMR (CDCl$_3$ + drop of CD$_3$OD, 200 MHz) δ 1.00 and 1.05 (6H, 2d, (CH$_3$)$_2$CH), 2.10 (1H, m), 3.62 (3H, s, NCH$_3$), 4.25 (2H, s, CH$_2$Ph), 4.15 (1H, m), 4.40 (2H, m), 7.28 (5H, m, C$_6$H$_5$).

EXAMPLE 11

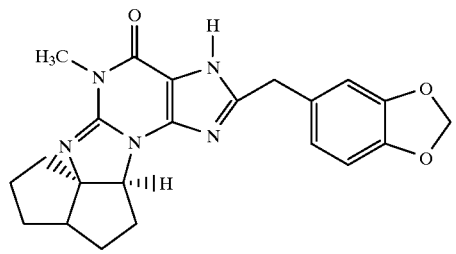

Step 1:

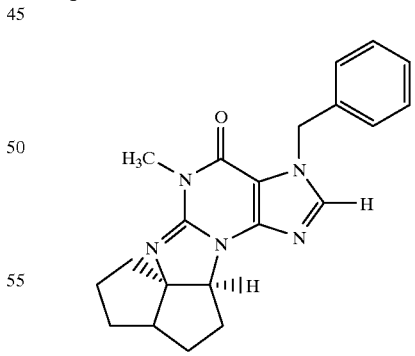

Heat a mixture of 2-choloro-1-methyl-7-(phenylmethyl) purin-6-one (1 g), 1-amino-7-hydroxybicyclo[3.3.0]octane hydrochloride (0.65 g), (i-pr$_2$NEt) (1.25) and NMP (3) in a sealed tube at 14° C. or 60 h. Cool the reaction to room temperature and pour into water. Collect the solid by filtration, dissolve it in CH$_2$Cl$_2$ and chromatograph on silica gel, eluting with CH$_2$Cl$_2$/CH$_3$OH (95/5) to give a solid. FAB MS 380 (m+H, 100%). Dissolve a portion of this solid (0.82 g) in CH$_2$Cl$_2$ (5 mL), and add SOCl$_2$ (0.5 mL). Stir the reaction mixture for 2 h, partition between NaHCO$_3$ and CH$_2$Cl$_2$. Wash the organic layer with brine, dry over MgSO$_4$, filter and concentrate to dryness to obtain a solid. EI MS (70 ev) 361 (M+, 100%).

Step 2:

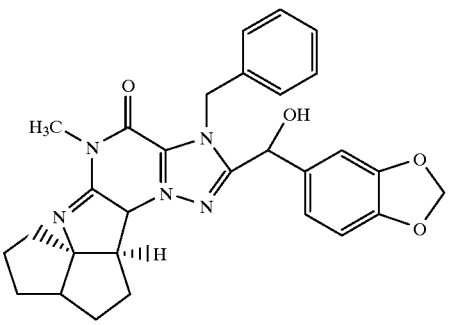

Add the product of Step 1 (0.36 g) to a solution of LDA (1.2 mmol) in THF (2 mL) at −78° C. Stir the reaction mixture for 0.5 h, then add a solution of piperonal (0.18 g) in THF and continue stirring at −78° C. for 1 h. Quench the reaction with HOAc (0.1 mL) and allow the reaction mixture to warm to room temperature, then partition between EtOAc and NaHCO$_3$. Wash the organic layer with brine, dry over MgSO$_4$, filter and concentrate to dryness to give a solid. EI MS (70 ev) 511 (M+, 100%).

Step 3: Place a mixture of the product of Step 2 (0.37 g), 20% palladium hydroxide on charcoal (0.15 g), EtOH (75 mL) and conc. HCl (0.6 mL) under a H$_2$ atmosphere (60 psi) for 60 h. Remove the catalyst by filtration through celite, concentrate the filtrate to dryness and partition the residue between NaHCO$_3$ and CH$_2$Cl$_2$. Wash the organic layer with brine, dry over MgSO4, filter and concentrate to dryness. Chromatograph this residue on silica gel, eluting with CH$_2$Cl$_2$/CH$_3$OH (95/5) to obtain the title compound as a colorless solid, mp 239–240° C., EI HRMS calc for C$_{22}$H$_{23}$N$_5$O$_3$ 405.1801, found 405.1806.

EXAMPLE 12

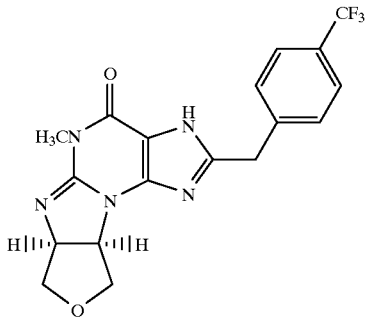

Step 1:

A: Add m-CPBA (9.5 g, 0.55 mol) to a solution of 1,4-dihydrofuran (3.8 mL, 0.050 mol) in CH$_2$Cl$_2$ (100 mL) at room temperature and stir for 16 h. Filter the solids, wash the filtrate with NaHCO$_3$ (sat.), dry over MgSO$_4$, and concentrate to give a clear oil (2.2 g, 51%). $^1$H-NMR (300 MHz, CDCl$_3$) δ 3.65 (d, 2H, J=10.5 Hz), 3.79 (s, 2H), 4.02 (d, 2H, J=10.6 Hz).

B: Heat R-(+)-α-methylbenzylamine (14 mL, 0.011 mol) with the product of Step A (10 g) and water (2 mL) at 100° C. for 24 h. Cool the reaction mixture and recrystallize the solid twice from CH$_2$Cl2-hexanes (1.2 g). HPLC showed>91% purity. $^1$H-NMR (300 MHz, CDCl$_3$) 81.37 (d, 3H, J=6.7 Hz), 1.90 (br s, 2H), 3.03–3.07 (m, 1H), 3.36 (dd, 1H, J=9.3, 4.1 Hz), 3.66 (dd, 1H, J=9.8, 2.4 Hz), 3.86–3.92 (m, 2H), 3.98 (dd, 1H, J=9.8, 4.7 Hz), 4.22–4.25 (m, 1H), 7.26–7.37 (m, 5H).

C: Heat the product of Step B (750 mg) with NH$_4$HCO$_2$ (820 mg) in refluxing CH$_3$OH (30 mL) over Pd/C (700 mg) for 1 h. Cool, filter, and concentrate the mixture (300 mg, 95%). [α]$^{25}$D=−11° (c 0.2, MeOH); $^1$H-NMR (300 MHz, CDCl$_3$) δ 2.40 (br s, 3H), 3.74–3.96 (m, 3H), 4.26–4.34 (m, 2H), 4.44–4.48 (m, 1H).

Step 2:

A: Stir 6-amino-3-methyl-5-(phenylmethyleneamino) pyrimidine-2,4-dione (2.46 g), 4-trifluoromethylphenylacetic acid (5.1 g) and DEC (4.8 g) in dry DMF at room temperature for 4 h. Pour the reaction mixture over ice, filter the solids and wash with Et$_2$O (3.80 g, 88%). $^1$H NMR (DMSO-d$_6$, 300 MHz) δ 3.00 (s, 3H), 3.58 (s, 2H), 4.51 (d, 1H, J=14 Hz), 4.59 (d, 1H, J=14 Hz), 6.27 (br s, 2H), 7.22–7.32 (m, 5H), 7.38 (d, 2H, J=8 Hz), 4.59 (d, 2H, J=8 Hz), 10.45 (br s, 1H).

B: Reflux the product of Step 2A (1.8 g) in POCl$_3$ (30 mL) for 16 h. Cool the reaction mixture and dilute with hexanes (600 mL). After 4 h, decant the liquid layer from the oily residue, dissolve the residue in CH$_2$Cl$_2$—CH$_3$OH (9-1), wash with NaHCO$_3$ (sat.), dry (MgSO$_4$), and concentrate. Purify the residue by flash chromatography, eluting with CHCl$_3$—CH$_3$OH (97-3) (700 mg, 36%). $^1$H NMR (CDCl$_3$, 300 MHz) δ 3.72 (s, 3H), 4.15 (s, 2H), 5.54 (s, 2H), 6.99 (d, 2H, J=7.9 Hz), 7.19–7.34 (m, 5H), 7.49 (d, 2H, J=7.9 Hz).

Step 3: Heat the product of Step 2B (0.68 g, 1.57 mmol), the product of Step 1C (0.28 g), and Et$_3$N (0.9 mL) in 20 mL of NMP at 120° C. for 16 h. Concentrate the mixture to remove NMP. Dissolve the residue in CH$_2$Cl$_2$, wash with NaHCO$_3$ (sat.), dry over MgSO$_4$, and concentrate. Purify the residue by flash chromatography, eluting with CHCl$_3$—CH$_3$OH (95-5) (320 mg, 54%). To a solution of the resultant compound (320 mg) and Et$_3$N (0.6 mL) in CH$_2$Cl$_2$ (25 mL), add, dropwise, CH$_3$SO$_2$Cl (0.12 mL) and stir for 16 h. Wash the solution with NaHCO$_3$ (sat.), dry (MgSO$_4$), and concentrate. Purify the resultant residue by flash chromatography, eluting with CHCl$_3$—CH$_3$OH (97-3) (250 mg, 78%). $^1$H NMR (CDCl$_3$, 300 MHz) δ 3.50 (s, 3H), 3.72–3.78 (m, 2H), 4.10 (s, 2H), 4.29 (d, 1H, J=9.2 Hz), 4.47 (d, 1H, J=11 Hz), 4.96–5.00 (m, 1H), 5.12–5.17 (m, 1H), 5.40 (d, 1H, J=16 Hz), 5.48 (d, 1H, J=16 Hz), 7.02–7.05 (m, 2H), 7.15 (d, 2H, J=8.3 Hz), 7.26–7.30 (m, 3H), 7.51 (d, 2H, J=8.4 Hz).

Step 4: Reflux the product of Step 3 (190 mg), NH$_4$HCO$_2$ (200 mg), and 10% Pd/C (150 mg) in CH$_3$OH (25 mL) for 1.5 h. Filter the mixture and wash the solids with CH$_2$Cl$_2$—CH$_3$OH (9-1). Combine the filtrate and the washings, wash with NaHCO$_3$ (sat.), dry (MgSO$_4$), and concentrate. Purify the resultant residue by flash chromatography, eluting with CHCl$_3$—CH$_3$OH (95-5) to obtain the title compound (100 mg) as a white solid. [α]$^{25}$D=+125° (c 0.4, EtOH); $^1$H NMR (CDCl$_3$, 300 MHz) δ 3.48 (s, 3H), 3.69–3.76 (m, 2H), 4.19 (d, 1H, J=10.5 Hz), 4.24 (s, 2H), 4.42 (d, 1H, J=11.3 Hz), 4.92–4.96 (m, 1H), 5.10–5.14 (m, 1H), 7.46 (d, 2H, J=8.0 Hz), 7.58 (d, 2H, J=8.0 Hz).

EXAMPLE 13

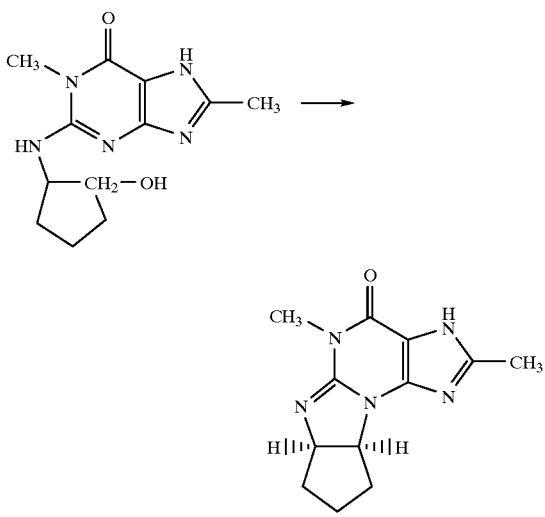

To a suspension of 1.5 g of the product of Preparation 5 in 45 ml CH$_2$Cl$_2$ at room temperature under N$_2$, add 1.7 ml of SOCl$_2$. Stir the suspension until the reaction is complete, about 18 hours. Remove the volatiles under vacuum, dissolve the residue in CH$_3$OH and treat with excess Na$_2$CO$_3$ plus NaHCO$_3$. Stir for 30 minutes and filter. Remove CH$_3$OH from the filtrate, dissolve the residue in CH$_3$CN, filter and remove CH$_3$CN under reduced pressure. Dissolve the foam thus obtained in water, stir with an anion exchange resin such as IRA 401 S OH resin® (trademark of the Rohm and Haas Chemical Company, Philadelphia, Pa.) for 20 minutes. Filter and concentrate the aqueous solution, dissolve the residue thus obtained in CH$_2$Cl$_2$ and pass through a silica plug with 5% CH$_3$OH in CH$_2$Cl$_2$ as eluant. Concentrate the eluant and crystallize the resultant foam from CH$_3$CN to obtain 0.9 g of the title compound, a solid.

$[\alpha]_D^{26}$=+155°; MS (FAB) 246 (M+H).

EXAMPLE 14

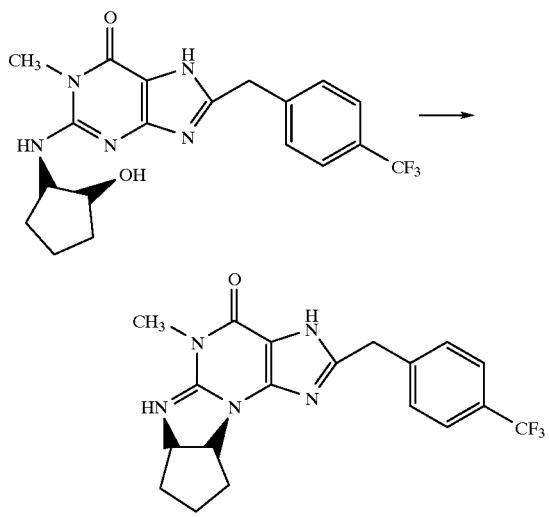

To a stirred solution of 86.5 g of the crude product of Preparation 5.1 in 1.3 L CH$_3$CN under N$_2$, kept at ~20° C. (water bath), add slowly 39 mL SOCl$_2$. Remove the water bath and stir vigorously at room temperature until complete reaction (about 12 to 18 hr) as judged by tlc. Concentrate under reduced pressure, take the resultant gum in a mixture of 1 L CH$_2$Cl$_2$ and 700 mL H$_2$O, stir this mixture and neutralize to a pH of 9.5 with slow addition of NH$_4$OH. Filter this mixture to remove solids and wash the solids with CH$_2$Cl$_2$. Combine the filtrate and the washes, separate the layers, treat the aqueous layer with ~1 g NaCl and then reextract with 2×500 mL CH$_2$Cl$_2$. Dry the combined organic layer (anhyd. MgSO$_4$) and concentrate in vacuo to obtain 74 g of a light brown solid. Slurry this solid in 225 mL EtOAc to obtain 35.6 g of off-white title compound. Concentrate the EtOAc filtrate and washes to obtain ~37 g of a brown-black solid. Subject this solid to silica gel column chromatography to obtain an additional 3.6 g of product.

Chromatograph the above product on silica gel to obtain a light tan solid as an analytical sample of the title compound. M.p. 235–237° C.; MS (EI): 389 (M+); Cl(NH$_4$): 390 (M+H); $[\alpha]_D^{25}$=+104° (c 1.0, MeOH).

Pharmaceutical Preparations

The compounds of formula I can be combined with a suitable pharmaceutical carrier to prepare a pharmaceutical composition suitable for parenteral or oral administration. Such pharmaceutical compositions are useful in the treatment of cardiovascular and pulmonary disorders such as mammalian hypertension and bronchoconstriction.

The effective daily antihypertensive dose (ED$_{50}$) of the present compounds will typically be in the range of about 1 to about 100 mg/kg of mammalian body weight, administered in single or divided doses. The exact dosage to be administered can be determined by the attending clinician and is dependent upon where the particular compound lies within the above cited range, as well as upon the age, weight and condition of the individual.

Generally, in treating humans in need of treatment for hypertension or bronchoconstriction, the present compounds can be administered in a dosage range of about 10 to about 500 mg per patient generally given a number of times per day, providing a total daily dosage of from about 10 to about 2000 mg per day.

The compositions of the present invention can be administered orally or parenterally. Typical injectable formulations include solutions and suspensions. Typical oral formulations include tablets, capsules, syrups, suspensions and elixirs. Also contemplated are mechanical delivery systems, e.g. transdermal dosage forms.

The typical acceptable pharmaceutical carriers for use in the formulations described above are exemplified by sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene glycol polymers; beta-cyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

Following are typical examples of oral and parenteral formulations, wherein the term "Active Ingredient" refers to a compound of formula I.

| Capsule | Amount (mg) | |
| --- | --- | --- |
| Active Ingredient | 250.0 | 125.0 |
| Lactose | 173.0 | 86.5 |
| Corn Starch | 75.0 | 37.5 |
| Magnesium Stearate | 2.0 | 1.0 |
| TOTAL | 500.0 | 250.0 |

Blend the active ingredient, lactose and corn starch until uniform; then blend the magnesium stearate into the resulting powder.

Encapsulate the mixture into suitably sized two-piece hard gelatin capsules.

| Tablet | Amount (mg) | |
| --- | --- | --- |
| Active Ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| TOTAL | 500.0 | 250.0 |

Blend the active ingredient with the lactose until uniform. Blend the smaller quantity of corn starch with the water and add the resulting corn starch paste then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

| Injectable Solution | mg/ml |
| --- | --- |
| Active Ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at a temperature of between 60° C. –70° C. and cool the solution to 20° C. –30° C., Charge and dissolve all other excipients and the active ingredient. Bring the solution to final volume, filter it through a sterilizing membrane and fill into sterile containers.

Biological Activity of 2-Benzyl Polycyclic Guanines

The present compounds are useful in inhibiting the phosphodiesterase enzymes. These phosphodiesterase enzymes are known to hydrolyze cGMP in smooth muscle. High levels of cGMP are associated with the relaxation of vascular smooth muscle, with a consequent subsequent reduction in blood pressure. Thus, it is believed that by inhibiting these phosphodiesterase enzymes, cGMP levels in muscle will be either maintained or increased, with a subsequent reduction in blood pressure. In vivo antihypertensive activity is determined orally in spontaneously hypertensive rats (SHR).

Phosphodiesterase inhibition in vitro:

Compounds are evaluated for inhibition of two phosphodiesterase enzymes which hydrolyze cyclic guanosine monophosphate (cGMP). The first enzyme, calcium-calmodulin dependent phosphodiesterase (CaM-PDE), is a partially pure enzyme aobtained from bovine aorta homogenates and purified by DEAE-cellulose and calmodulin-affinity chromatography. The enzyme is activated several fold by Ca-calmodulin and is selective for cGMP, although it will also hydrolyze cAMP. The second enzyme, cGMP phosphodiesterase (cGMP-PDE), is a homogeneous enzyme obtained from bovine lung and purified by ion-exchange chromatography, gel filtration, and sucrose gradient centrifugation. cGMP-PDE is highly selective for cGMP. Bovine aorta homogenates and primary cultures of bovine aortic endothelial and vascular smooth muscle cells contain an enzyme with properties very similar to the lung isozyme.

The enzyme assay is performed using a Biomek Automated Pipetting Station. Compounds are dissolved in distilled water or DMSO and diluted with 10% DMSO. Compounds are tested at several concentrations at log intervals, typically 0.1, 1.0, 10, and 100 $\mu$M final concentration.

Assays contain the following components:

1 $\mu$M substrate $^3$H-cGMP 50 mM Tris-HCl, pH 7.5, 5 mM $MgCl_2$ 0.5 mg/ml snake venom alkaline phosphatase 0.1 $\mu$M Calmodulin and 1 mM $CaCl_2$ (for CaM-PDE only)

Assays are initiated by addition of enzyme and stopped by addition of 10 mM isobutylmethylxanthine, a general phosphodiesterase inhibitor. Assays are performed for 25 minutes at room temperature to achieve 5–10% hydrolysis of substrate. The negatively charged substrates are then separated from guanosine by binding to an anion-exchange resin (AG1-X8) and centrifugation or filtration, and the product is quantitated by scintillation counting in counts per minute (cpm) of the remaining soluble material. Percent inhibition is calculated as follows:

% Inhibition=100-[(cpm compound-blank)/(cpm control-blank)X100]

Activity is expresssed as the $IC_{50}$ value, ie. the concentration required to inhibit activity of enzyme by 50 per cent.

Antihypertensive activity in rats

The ability of the compounds of the present invention to lower blood pressure can be assessed in vivo in conscious spontaneously hypertensive rats (SHR). SHR males are purchased from Taconic Farms, Germantown, N.Y. and are approximately 16–18 weeks old when anesthetized with ether. The caudal (ventral tail) artery is cannulated with polyethylene tubing (PE50) and blood pressure and heart rate are recorded as described by Baum, T. et. al, J. Cardiovasc. Pharmacol. Vol 5, pp. 655–667, (1983). Rats are placed into plastic cylindrical cages where they rapidly recover consciousness. Blood pressure and heart rate are allowed to stabilize for approximately 90 minutes prior to compound administration. Compounds are administered orally as solutions or suspensions in 0.4% aqueous methylcellulose vehicle via a feeding needle. The compound or 0.4% aqueous methylcellulose vehicle are given in a volume of 4 ml/kg to SHRs that had been fasted overnight. Activity is expressed as the fall in mean blood pressure (MBP) in millimeters of mercury (mm Hg). Compound-induced changes are compared with the changes in an appropriate placebo group. "NT" means that the compound was not tested in that assay.

| ACTIVITY OF 2-BENZYL-TETRACYLCLIC GUANINES | | | |
|---|---|---|---|
| | PDE IC$_{50}$ | SHR Antihypertensive | |
| Example Number | CaM ($\mu$M) | Dose (mpk) | Fall in MBP (mmHg) |
| 1 | 0.1 | 10 | 47 |
| 1A | <0.1 | 10 | 49 |
| 1B | 0.2 | 10 | 61 |
| 1C | 0.6 | 10 | 40 |
| 2 | <0.1 | 10 | 40 |
| 2A | 0.7 | 3 | 19 |
| 2B | 0.4 | 3 | 30 |
| 3 | <0.1 | 10 | 21 |
| 3A | 0.1 | 10 | 42 |
| 3B | 0.6 | 3 | 28 |
| 3C | 0.2 | 3 | 23 |
| 3D | NT | 3 | 28 |
| 3E | 0.9 | 10 | 29 |
| 3F | 0.8 | 10 | 34 |
| 3G | 0.3 | 3 | 28 |
| 3H | <0.1 | 3 | 27 |
| 4 | NT | 3 | 32 |
| 5 | NT | 3 | 33 |
| 6 | 0.48 | 3 | 19 |
| 7 | 0.65 | 3 | 27 |
| 8 | 0.1 | 10 | 40 |
| 9 | 0.3 | 10 | 47 |
| 10 | 0.1 | 10 | 39 |
| 11 | 0.2 | 10 | 59 |
| 12 | 3.0 | 3 | 20 |

The activities of cis-5,6a,7,8,9,9a-hexahydro-5-methyl-2-phenylmethyl)cyclopent[4,5]imidazo[2,1b]purin-4(3H)-one (Compound A) and cis-5,6a,7,8,9,9a-hexahydro-5-methylcyclopenta-[4,5]imidazo[2,1-b]-purin-4(3H)-one (Compound B), compounds specifically disclosed in WO91/19717, are as follows:

| Cpd. | PDE IC$_{50}$: | SHR: |
|---|---|---|
| A | CaM: 0.2 $\mu$M | fall in MBP at 25 mpk: 6 mmHg |
| B | CaM: 33 $\mu$M | fall in MBP at 25 mpk: 32 mmHg |
| | | fall in MBP at 10 mpk: 8 mmHg |

We claim:
1. A compound having the structural formula

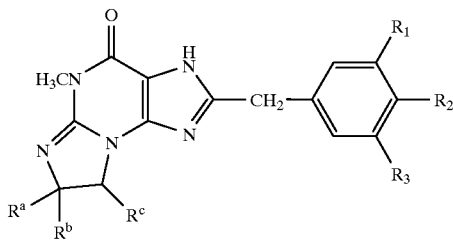

or a pharmaceutically acceptable salt thereof, wherein:
$R_1$, $R_2$ and $R_3$ are independently selected from the group consisting of hydrogen, lower alkyl, lower alkoxy, halogeno, hydroxy, (di-lower alkyl)amino, 4-morpholinyl, 1-pyrrolidinyl, 1-pyrrolyl, —CF$_3$, —OCF$_3$, phenyl and methoxyphenyl; or $R_1$ and $R_2$ together are methylenedioxy; or $R_1$ and $R_2$ together with the carbon atoms to which they are attached form a benzene ring; and $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5–7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5–7 carbons.

2. A compound of claim 1 wherein $R_1$ and $R_3$ are each hydrogen.

3. A compound of claim 1 wherein $R_1$ and $R_3$ are each hydrogen and $R_2$ is hydrogen, —CF$_3$, —OCF$_3$, methyl, methoxy, fluoro, phenyl, methoxyphenyl, dimethylamino, 1-pyrrolidinyl or 1-pyrrolyl; or wherein $R_1$ and $R_2$ together form a methylenedioxy group and $R_3$ is hydrogen.

4. A compound of claim 1 wherein $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5 carbons.

5. A compound of claim 1 wherein $R^a$ is lower alkyl, $R^b$ is lower alkyl or hydrogen, and $R^c$ is hydrogen; $R^a$ and $R^b$ and the carbon atom to which they are attached form a saturated ring of 5 carbons and $R^c$ is hydrogen; or $R^a$ is hydrogen and $R^b$ and $R^c$, together with the carbon atoms to which they are attached, form a saturated ring of 5 carbons.

6. A compound of claim 1 having the structural formula

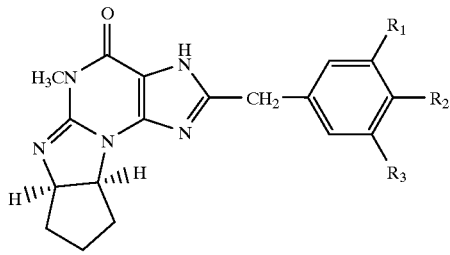

wherein $R^a$ is hydrogen and $R^b$ and $R^c$, together with the carbon atoms to which they are attached, form a saturated ring of 5 carbons, and wherein $R_1$, $R_2$ and $R_3$ are as defined in the following table:

| $R_1$ | $R_2$ | $R_3$ |
|---|---|---|
| H | H | H |
| —OCH$_3$ | H | H |
| H | F | H |
| H | —OCH$_3$ | H |
| H | OH | H |
| H | —CH$_3$ | H |
| H | (CH$_3$)$_2$N— | H |
| —OCH$_3$ | —OCH$_3$ | —OCH$_3$ |
| —OCH$_3$ | —OCH$_3$ | H |
| —CF$_3$ | H | H |
| H | C$_6$H$_5$— | H |

-continued

| $R_1$ | $R_2$ | $R_3$ |
|---|---|---|
| H | —OCF$_3$ | H |
| H | —N(pyrrolidine) | H |
| H | —N(pyrrole) | H |
| 3,4-OCH$_2$O— | | H |
| H | —N(morpholine) | H |
| H | —C$_6$H$_4$-OCH$_3$ (para) | H |
| $R_1$ and $R_2$, together with the carbon atoms to which they are attached form a benzene ring | | H |
| H | Cl | H |

7. A compound of claim 1 selected from the group consisting of:

2'-benzyl-5'-methyl-spiro[cyclopentane-1',7' (8'H)-[3'H]-imidazo[2,1-b]purin]-4'-(5'H)-one;

2'-benzyl-5,7,7-trimethyl-3H-imidazo[2,1-b]purin-4-(5H)-one;

(+)-2-benzyl-7,8-dihydro-5-methyl-7-(1-methylethyl)-1H-imidazo[2,1-b]-purin-4(5H)-one;

(+,−)-6a, 7, 8, 9, 9a, 10, 11, 11a-octahydro-5-methyl-2-(3,4-methylene-dioxyphenylmethyl)-3H-pentalen[6a,1:4,5]imidazo[2,1-b]purin-4(5H)-one; and (+)-cis-6a, 7, 9, 9a-tetrahydro-5-methyl-2-[4-(trifluoromethyl)-phenylmethyl]-3H-furo[3', 4':4,5]imidazo[2,1-b]purin-4(5H)-one.

8. A pharmaceutical composition comprising an effective amount of a compound of claim 1 in a pharmaceutically acceptable carrier.

9. A method of treating hypertension, angina, bronchoconstriction, restenosis post angioplasty, atherosclerosis, ischemia, peripheral vascular diseases, or diseases benefitting from platelet inhibition, or for maintaining guanosine 3':5'-cyclic monophosphate (cGMP) levels, comprising administering an effective amount of a compound of claim 1 to a mammal in need of such treatment.

* * * * *